(12) United States Patent
Sakamoto et al.

(10) Patent No.: US 8,075,904 B2
(45) Date of Patent: Dec. 13, 2011

(54) HIGH ASPECT RATIO TEMPLATE AND METHOD FOR PRODUCING SAME FOR CENTRAL AND PERIPHERAL NERVE REPAIR

(75) Inventors: Jeff S. Sakamoto, East Lansing, MI (US); Mark Henry Tuszynski, La Jolla, CA (US); Thomas Gros, Fairfield, CA (US); Christina Chan, Okemos, MI (US); Sumit Mehrotra, East Lansing, MI (US)

(73) Assignees: California Institute of Technology, Pasadena, CA (US); The Regents of University of California, Oakland, CA (US); Board of Trustees of Michigan State University, East Lansing, MI (US)

( * ) Notice: Subject to any disclaimer, the term of this patent is extended or adjusted under 35 U.S.C. 154(b) by 403 days.

(21) Appl. No.: 12/203,068

(22) Filed: Sep. 2, 2008

(65) Prior Publication Data

US 2009/0202605 A1    Aug. 13, 2009

Related U.S. Application Data

(63) Continuation-in-part of application No. 11/200,982, filed on Aug. 10, 2005, now Pat. No. 7,837,913.

(60) Provisional application No. 60/967,091, filed on Aug. 31, 2007, provisional application No. 60/680,435, filed on May 12, 2005, provisional application No. 60/639,462, filed on Dec. 28, 2004, provisional application No. 60/600,454, filed on Aug. 11, 2004.

(51) Int. Cl.
*C61F 13/00* (2006.01)
*C61F 2/00* (2006.01)
*B01D 39/00* (2006.01)
*B29B 17/00* (2006.01)
*B29B 44/04* (2006.01)

(52) U.S. Cl. ............. 424/422; 422/423; 210/500.22; 210/500.34; 210/500.35; 264/48; 264/344; 623/1; 623/49

(58) Field of Classification Search .......... 424/422, 424/423, 97.7; 435/375, 395; 514/252.5; 536/57; 623/16.11, 890.1, 1.49; 264/48, 264/49, 344; 210/500.22, 500.34, 500.35, 210/50, 509; 428/357, 311.51; 977/896
See application file for complete search history.

(56) References Cited

U.S. PATENT DOCUMENTS 4,407,959 A * 10/1983 Tsuji et al. ............. 204/403.1
(Continued)

OTHER PUBLICATIONS

Berry, A. D., et al., Fabrication of GaAs and InAs wires in Nanochannel Glass, Appl. Phys. Lett 69(19):2846-2848 (1996).

(Continued)

*Primary Examiner* — Ana Fortuna
(74) *Attorney, Agent, or Firm* — Seth D. Levy; Davis Wright Tremaine LLP

(57) ABSTRACT

Millimeter to nano-scale structures manufactured using a multi-component polymer fiber matrix are disclosed. The use of dissimilar polymers allows the selective dissolution of the polymers at various stages of the manufacturing process. In one application, biocompatible matrixes may be formed with long pore length and small pore size. The manufacturing process begins with a first polymer fiber arranged in a matrix formed by a second polymer fiber. End caps may be attached to provide structural support and the polymer fiber matrix selectively dissolved away leaving only the long polymer fibers. These may be exposed to another product, such as a biocompatible gel to form a biocompatible matrix. The polymer fibers may then be selectively dissolved leaving only a biocompatible gel scaffold with the pores formed by the dissolved polymer fibers. The scaffolds may be used in, among other applications, the repair of central and peripheral nerves. Scaffolds for the repair of peripheral nerves may include a reservoir for the sustained release of nerve growth factor. The scaffolds may also include a multifunctional polyelectrolyte layer for the sustained release of nerve growth factor and enhance biocompatibility.

32 Claims, 21 Drawing Sheets
(4 of 21 Drawing Sheet(s) Filed in Color)

U.S. PATENT DOCUMENTS

| | | | | |
|---|---|---|---|---|
| 5,798,113 | A * | 8/1998 | Dionne et al. | 424/422 |
| 5,800,828 | A * | 9/1998 | Dionne et al. | 424/422 |
| 5,856,367 | A | 1/1999 | Barrows et al. | |
| 6,203,573 | B1 * | 3/2001 | Walter et al. | 623/16.11 |
| 6,231,605 | B1 | 5/2001 | Ku | |
| 6,534,084 | B1 | 3/2003 | Vyakarnam et al. | |
| 6,673,285 | B2 | 1/2004 | Ma | |
| 6,800,753 | B2 * | 10/2004 | Kumar | 536/57 |
| 6,890,335 | B2 * | 5/2005 | Grabowski et al. | 606/71 |
| 6,921,508 | B2 | 7/2005 | Latini et al. | |
| 6,974,823 | B2 * | 12/2005 | Hamilton | 514/307 |
| 7,087,200 | B2 | 8/2006 | Taboas et al. | |
| 7,253,169 | B2 * | 8/2007 | Wu et al. | 514/252.05 |
| 7,270,813 | B2 | 9/2007 | Shimp et al. | |
| 7,369,900 | B2 * | 5/2008 | Zdravkovic | 607/118 |
| 7,384,786 | B2 * | 6/2008 | Freyman et al. | 435/395 |
| 7,431,869 | B2 | 10/2008 | Haggard et al. | |
| 7,575,759 | B2 | 8/2009 | Murphy et al. | |
| 7,579,189 | B2 * | 8/2009 | Freyman et al. | 435/395 |
| 7,655,463 | B2 * | 2/2010 | Sah et al. | 435/375 |
| 7,670,797 | B2 | 3/2010 | Vacanti et al. | |
| 7,709,020 | B2 * | 5/2010 | Berstein et al. | 424/423 |
| 7,736,309 | B2 * | 6/2010 | Miller et al. | 600/300 |
| 7,837,913 | B2 * | 11/2010 | Sakamoto et al. | 264/48 |
| 2010/0055144 | A1 | 3/2010 | Sakamoto et al. | |

OTHER PUBLICATIONS

Martin-Gonzalez, M., et al., Direct Electrodeposition of Highly Dense 50 nm $Bi_2Te_{3-y}Se_y$ Nanowire Arrays, Nano Letters, 3(7):973-977 (2003).

Penner, R.M., et al., Preparation and Electrochemical Characterization of Ultramicroelectrode Ensembles, Anal. Chem. 59:2625-2630 (1987).

Thurn-Albrecht, T., et al., Ultrahigh-Density Nanowire Arrays Grown in Self-Assembled Diblock Copolymer Templates, Science, 209:2126-2129 (2000).

* cited by examiner

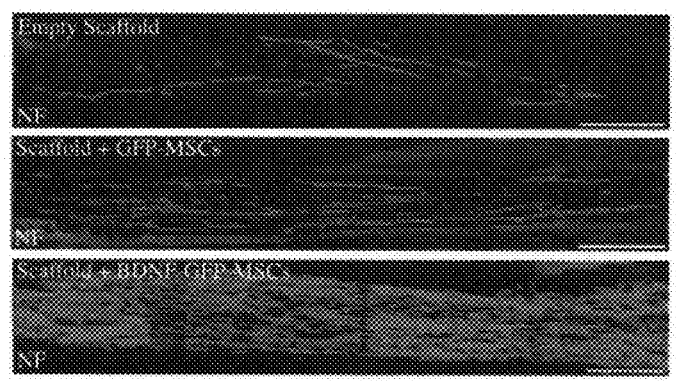
FIG. 6A
FIG. 6B
FIG. 6C
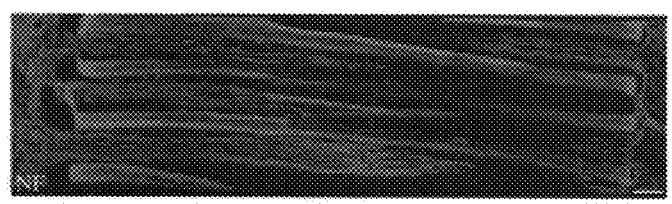
FIG. 7

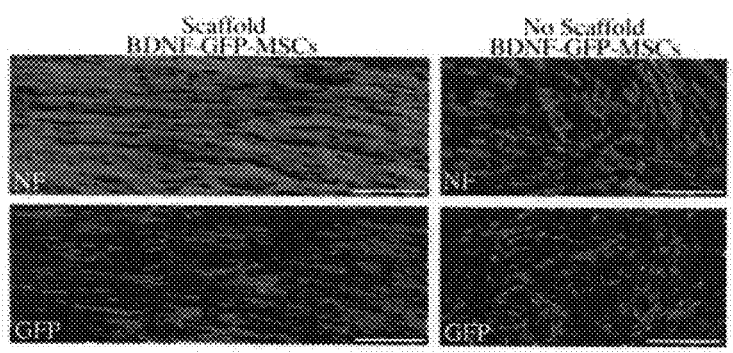
FIG. 8A
FIG. 8B
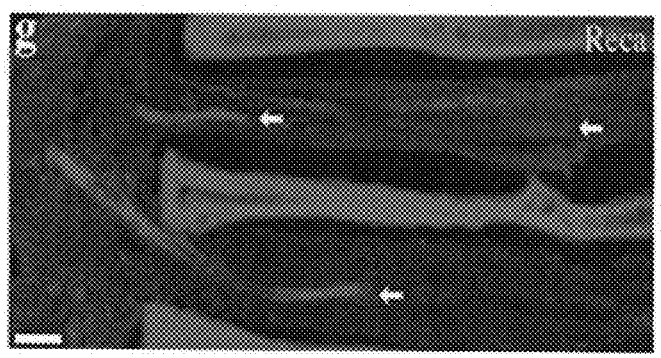
FIG. 9

FIG. 14
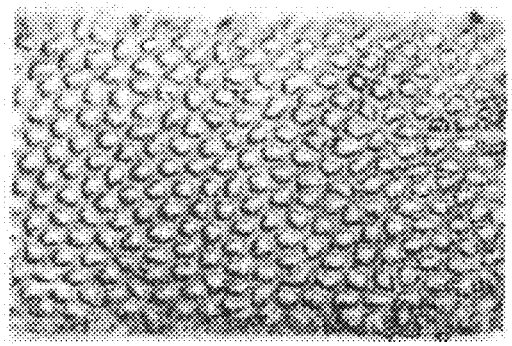
(a)
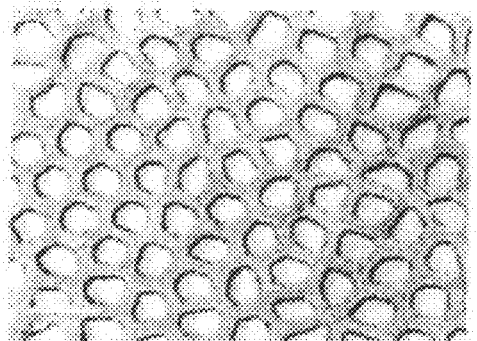
(b)
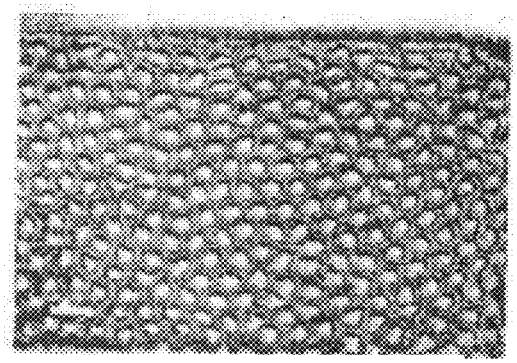
(c)
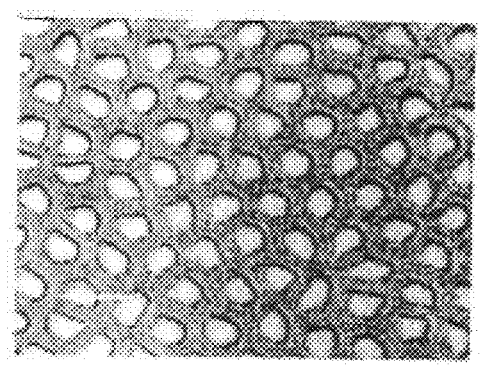
(d)
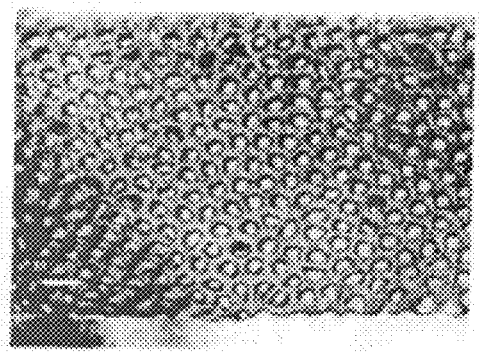
(e)
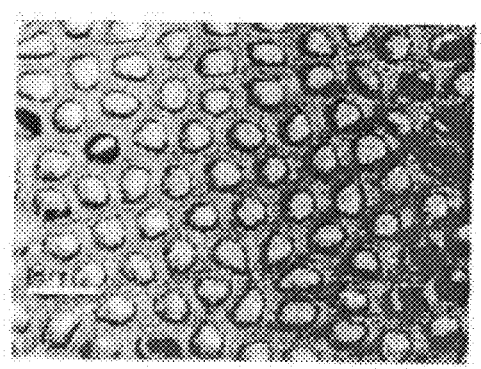
(f)

FIG. 15
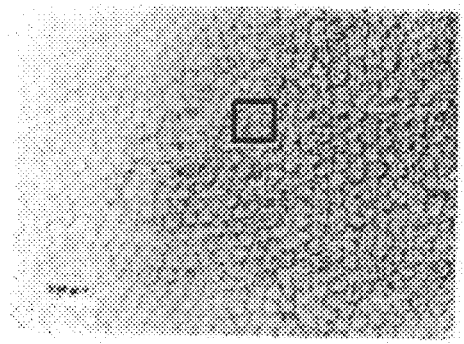
(a)
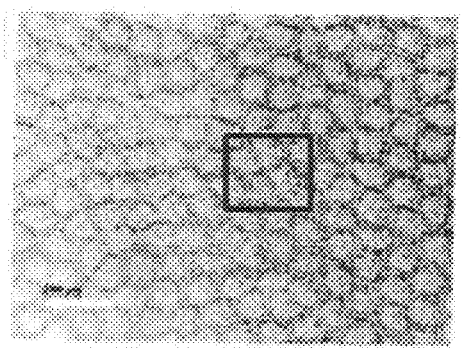
(b)
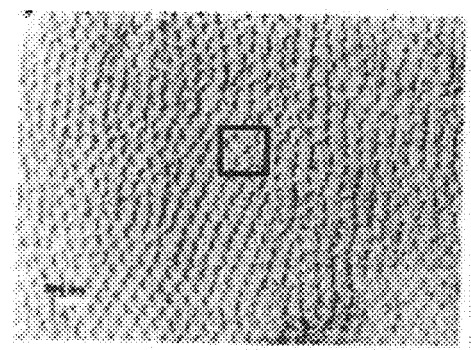
(c)
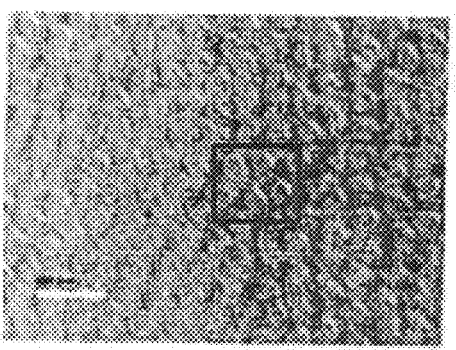
(d)
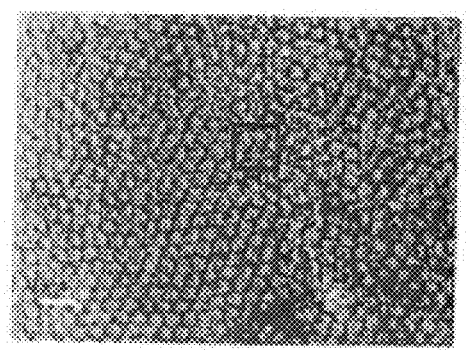
(e)
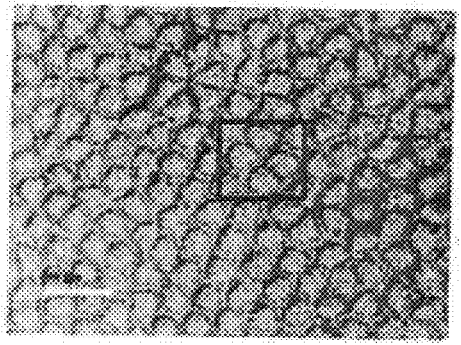
(f)

HIGH ASPECT RATIO TEMPLATE AND METHOD FOR PRODUCING SAME FOR CENTRAL AND PERIPHERAL NERVE REPAIR

CROSS-REFERENCE TO RELATED APPLICATIONS

This application is a continuation-in-part of, and claims the benefit of priority of, U.S. application Ser. No. 11/200,982, filed Aug. 10, 2005, which claimed the benefit of priority of U.S. Provisional Application Ser. No. 60/600,454, filed Aug. 11, 2004, U.S. Provisional Application Ser. No. 60/639,462, filed Dec. 28, 2004, and U.S. Provisional Application Ser. No. 60/680,435, filed May 12, 2005. This application also claims the benefit of priority of co-pending U.S. Provisional Application Ser. No. 60/967,091, filed Aug. 31, 2007. The various priority applications are incorporated by reference herein as if set forth in their entirety.

STATEMENT REGARDING FEDERALLY SPONSORED RESEARCH OR DEVELOPMENT

The invention described herein was made in the performance of work under a NASA contract, and is subject to the provisions of public law 96-517 (35 U.S.C. §202) in which the Contractor has elected to retain title.

BACKGROUND OF THE INVENTION

1. Field of the Invention

The present invention is directed generally to microtechnology/nanotechnology and, more particularly, to fabricating biocompatible scaffolds with highly-ordered arrays of high-aspect ratio conduits and to fabricating nano-scale templates with highly-ordered arrays of high-aspect ratio conduits. The biocompatible scaffolds may be used in, among other applications, central and peripheral nerve repair.

2. Description of the Related Art

Conventional machining technologies have long been used to manufacture components for a variety of applications. However, conventional techniques are limited to certain types of materials (e.g., metal) and face fundamental limitations in the size of the components.

For example, it is desirable in some applications to have a structure that contains pores or conduits with a very small diameter. Many applications that require small pore size also require a relatively long pore length. Known techniques for creating such high-aspect ratio pores are not suitable for a number of reasons. Mechanical drilling is not gentle enough to fabricate structures with thin walls and cannot be used to achieve holes with a diameter <100 micrometers (µm).

Photolithography is not capable of producing features having out of plane depth exceeding 0.1 millimeters (mm). Standard photolithographic techniques, used for patterning semiconductor devices, cannot produce high-aspect ratio pores. The maximum achievable pore length of a standard photolithographic patterning is typically <0.1 millimeters (mm), and is limited by the maximum achievable thickness of photo resist. Alternatively, LIGA is a lithography process utilizing synchrontron radiation that may be capable of generating higher aspect ratio pores, but is cost prohibitive. This is particularly important if the nano-scale device is disposable.

Laser drilling is generally not compatible with bio-polymer gels, which may be as much as 97% water. In addition, it is difficult to achieve high intensity at a spot size <100 µm with laser drilling. Dye extrusion is also an incompatible process for bio-polymer gels at a length scale in the 10 micron range.

Accordingly, it can be appreciated that there is a significant need for a process compatible with materials and capable of patterning high-aspect ratio features ranging from the nanometer to millimeter scale. The present invention provides this, and other advantages as will be apparent from the following detailed description and accompanying figures.

BRIEF DESCRIPTION OF THE SEVERAL VIEWS OF THE DRAWING(S)

The file of this patent contains at least one drawing executed in color. Copies of this patent with color drawing(s) will be provided by the patent and Trademark Office upon request and payment of the necessary fee.

FIGS. 6A-6C are photographs of slides demonstrating nerve growth using the biocompatible scaffold of FIG. 1.

FIG. 7 is a photograph of a slide demonstrating nerve growth in multiple channels of the biocompatible scaffold of FIG. 1

FIGS. 8A-8B are photographs of slides demonstrating an improvement of nerve growth using the biocompatible scaffold of FIG. 1.

FIG. 9 is a photograph of a slide demonstrating vascular regeneration in multiple channels of the biocompatible scaffold of FIG. 1

FIG. 14 a-f shows a 100/200 scaffold cross-sectional analysis of a 7.5 mm long scaffold. Lower magnification micrographs a, c, and e are taken at 2, 3.75 and 5.5 mm along the longitudinal axis of the scaffold, respectively. The scale bar represents 200 microns. Higher magnification micrographs b, d and f are also taken at 2, 3.75 and 5.5 mm along the longitudinal axis of the scaffold, respectively.

FIG. 15 a-f shows a 50/150 scaffold cross-sectional analysis of a 7.5 mm long scaffold. Lower magnification micrographs a, c, and e are taken at 2, 3.75 and 5.5 mm along the longitudinal axis of the scaffold, respectively. The scale bar represents 200 microns. Higher magnification micrographs b, d and f are also taken at 2, 3.75 and 5.5 mm along the longitudinal axis of the scaffold, respectively. The white boxes highlight a cluster of four channels that extend from end to end.

Figure 16:
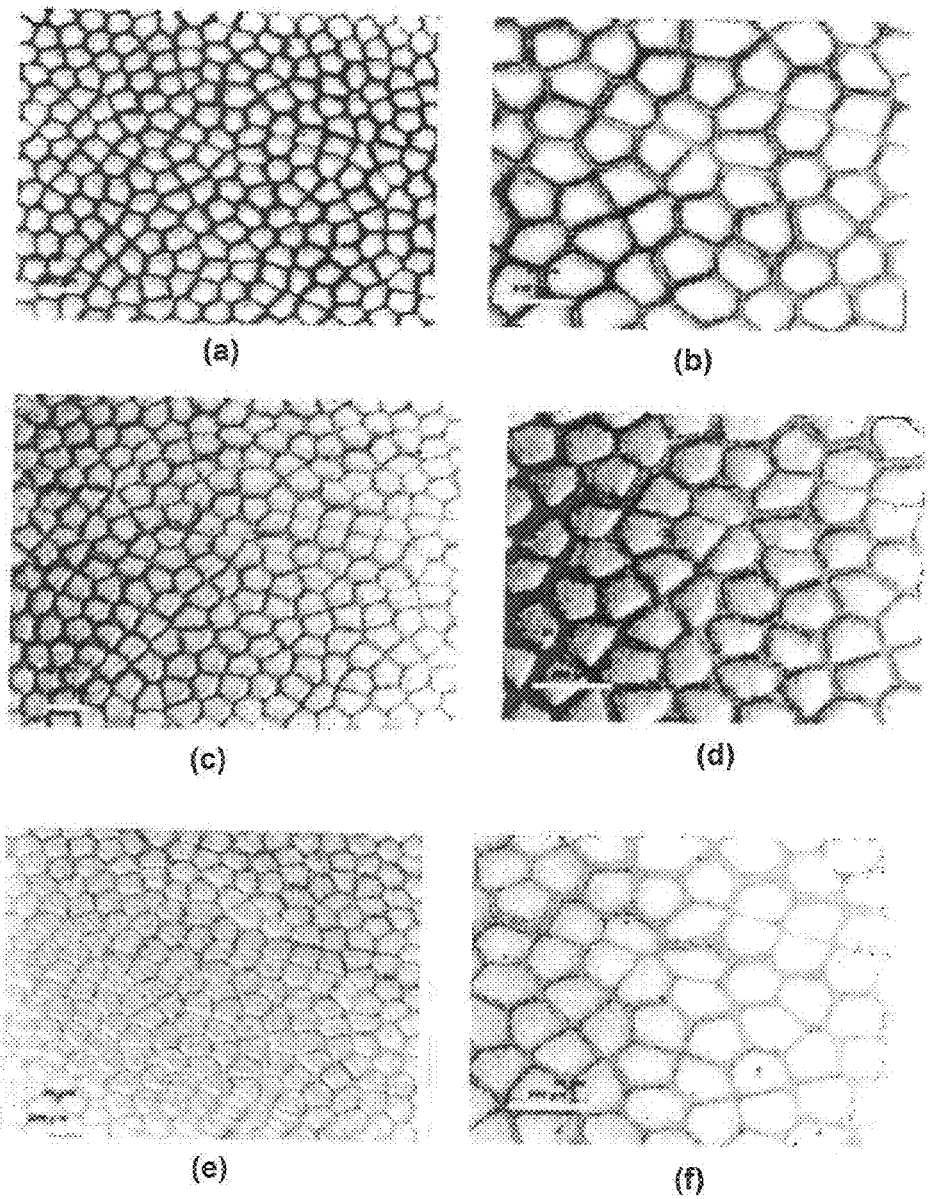

FIG. 16 a-f shows a 40/280 scaffold cross-sectional analysis of a 7.5 mm long scaffold. Lower magnification micrographs a, c, and e are taken at 2, 3.75 and 5.5 mm along the longitudinal axis of the scaffold, respectively. The scale bar represents 200 microns. Higher magnification micrographs b, d and f are also taken at 2, 3.75 and 5.5 mm along the longitudinal axis of the scaffold, respectively.

Figure 17:
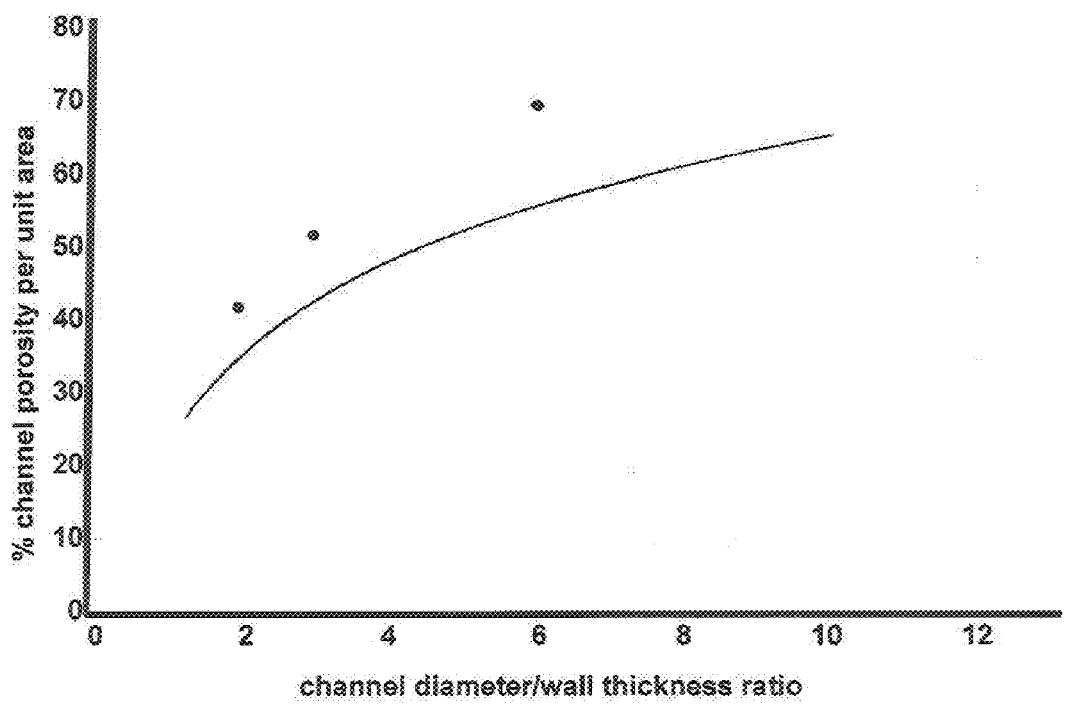

FIG. 17 is a plot comparing the effect of channel porosity per unit volume of scaffold as a function of the ratio of channel diameter to wall thickness. The solid line represents the values predicted by the hard cylinder model for close packed arrays of hard cylinders.

Figure 18:
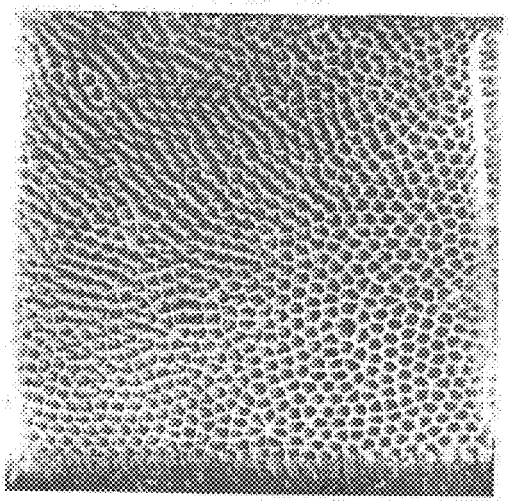

FIG. 18 shows a 1 cm by 1 cm by 1 cm cubic scaffold fabricated using 40/280 templates.

Figure 19:
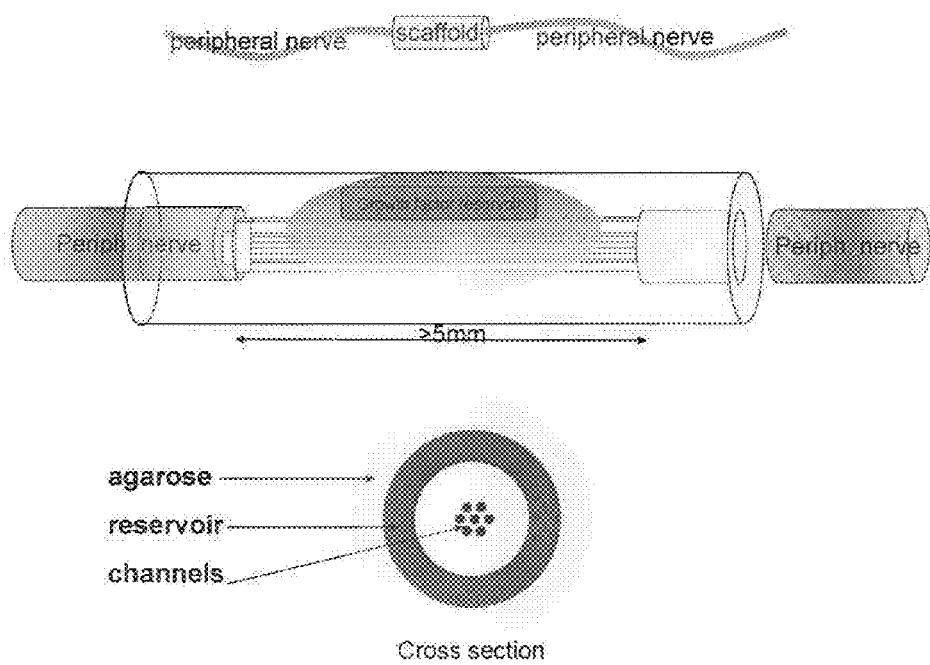

FIG. 19 shows time release scaffolds. The upper portion of the figure illustrates the location and configuration of the scaffold in relation to the peripheral nerve to be repaired. The middle portion of the figure illustrates the detailed features of the scaffold in interaction with the peripheral nerve being repaired. The bottom portion of the figure shows the cross-section of the scaffold.

Figure 20:
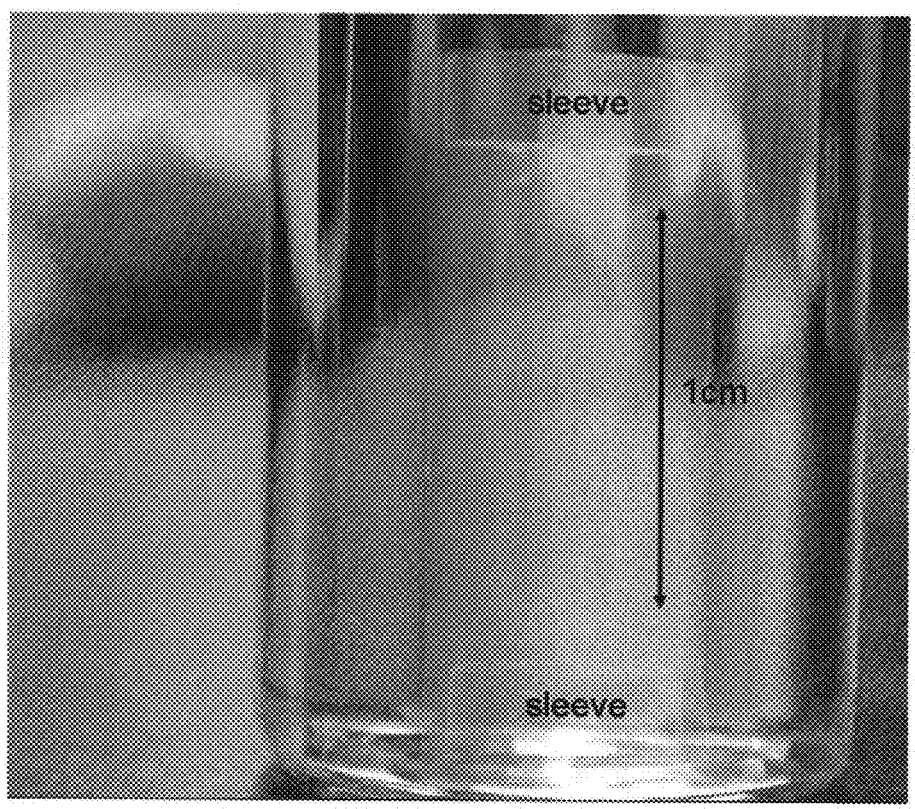

FIG. 20 shows a time release scaffold with open-ended sleeves and a hexagonal close-packed array of channels at the center.

Figure 21:
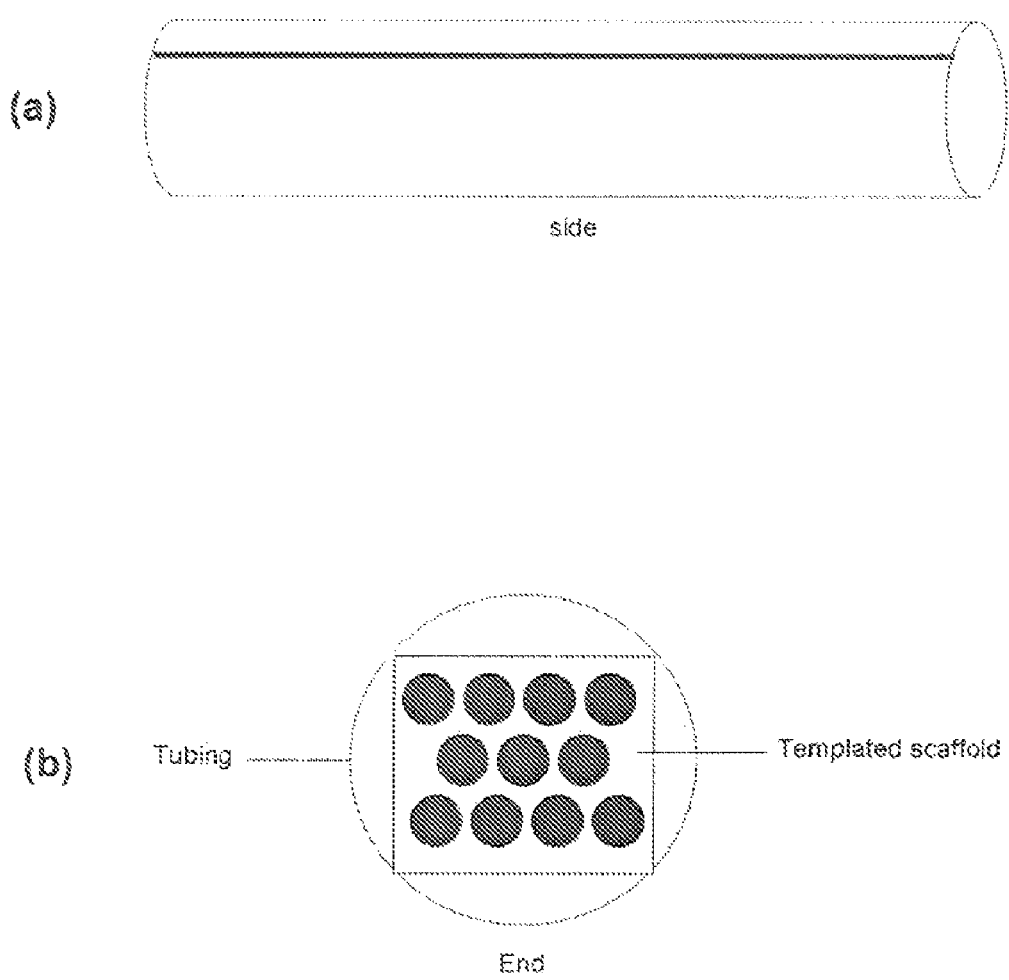

FIG. 21 a-b shows a TYGON® (polyvinyl chloride thermoplastic polymer) outer reinforcing tube for the biocompatible agarose scaffold. The TYGON® (polyvinyl chloride thermoplastic polymer) tube prevents fracture of the scaffold and facilitates the attachment of the tissue to be repaired to the scaffold. FIG. 21a shows a side view of the reinforcing tube. FIG. 21b shows an end view with the biocompatible agarose scaffold being deployed inside the TYGON® (polyvinyl chloride thermoplastic polymer) outer reinforcing tube.

Figure 22:
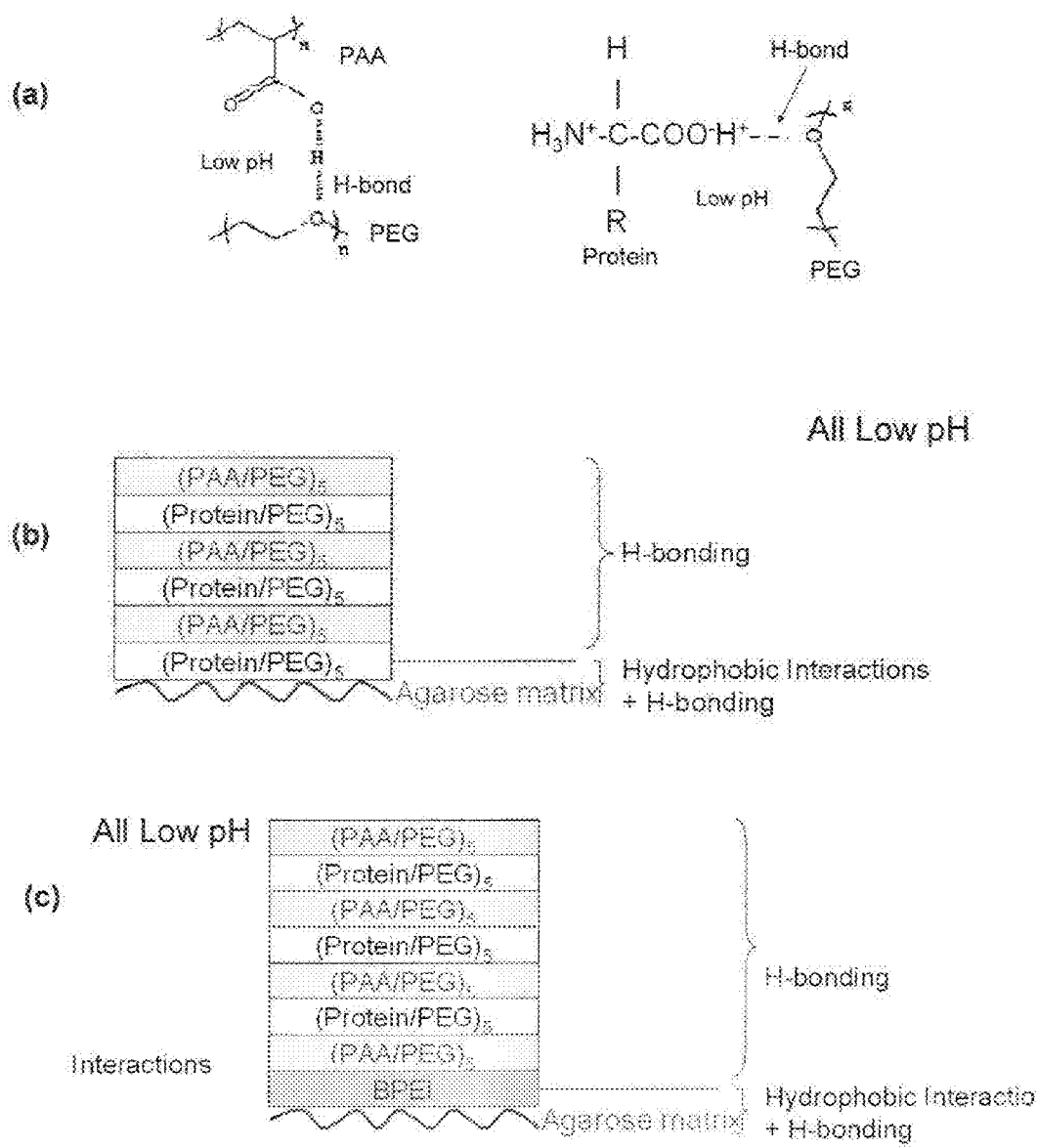

FIG. 22 a-c shows the protein release characteristics of two separate Multifunctional Polyelectrolyte Layers (MPL) when deployed on the biocompatible scaffolds of the present invention. FIG. 22a shows the chemical structures of the MPL. FIG. 22b shows an MPL initiated with protein and FIG. 22c shows an MPL initiated with branched polyethylenimine (BPEI).

Figure 23:
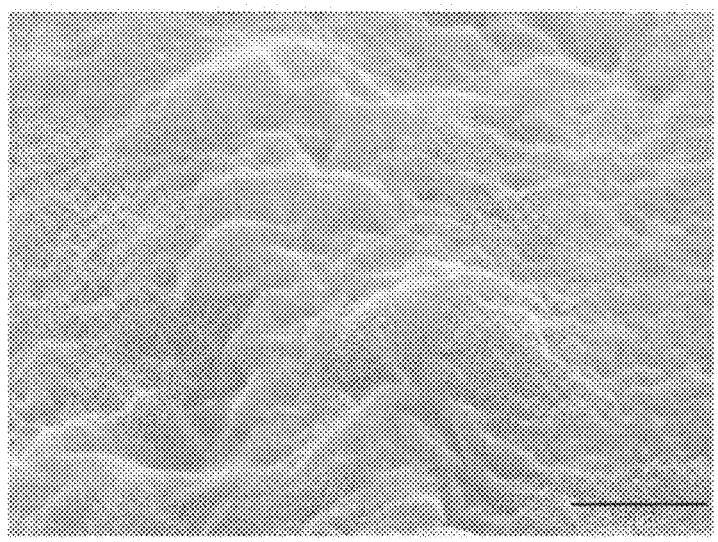

FIG. 23 is an SEM micrograph image of a BPEI(PAA/PEG)$_5$[(PAA/BSA)$_{50}$] MPL which was fabricated onto 3% (w/v) agarose.

Figure 24:
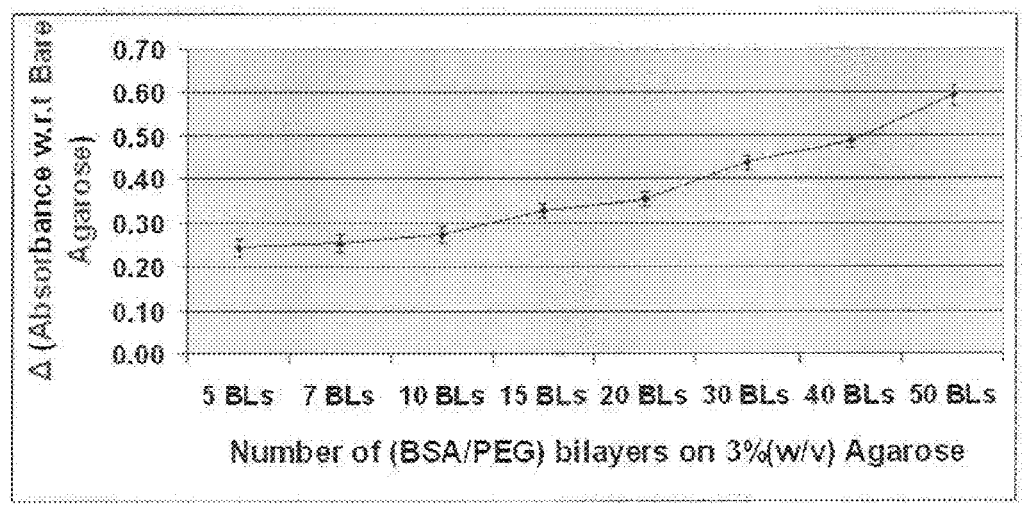

FIG. 24 shows the change in absorbance of a BPEI(PAA/PEG)$_5$[(PAA/BSA)$_n$] MPL-loaded hydrogel as a function of an increasing number of PAA/BSA layers.

Figure 25:
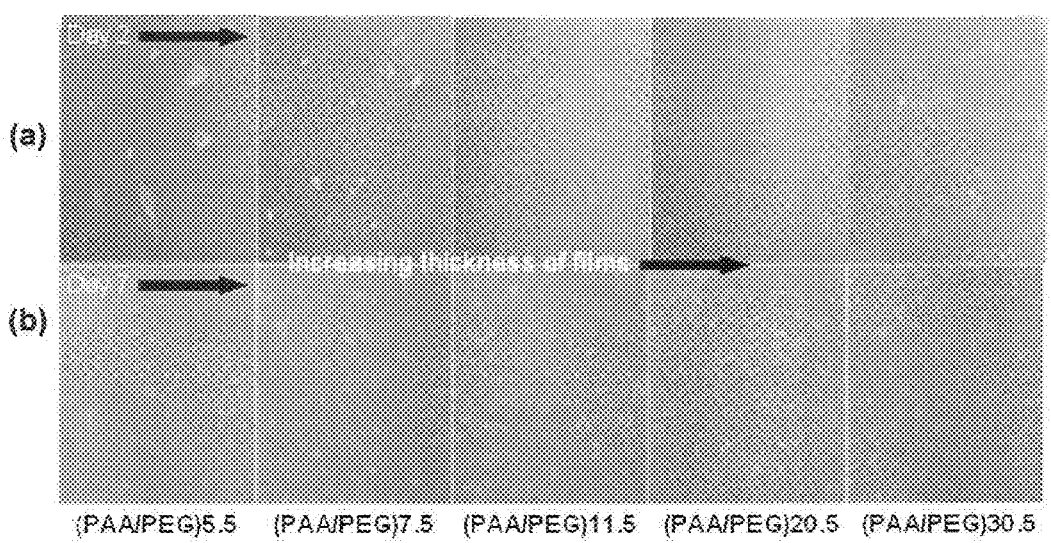

FIG. 25 a-b shows fibroblast adhesion behavior on PAA/PEG multilayers deposited on a plane glass substrate.

Figure 26:
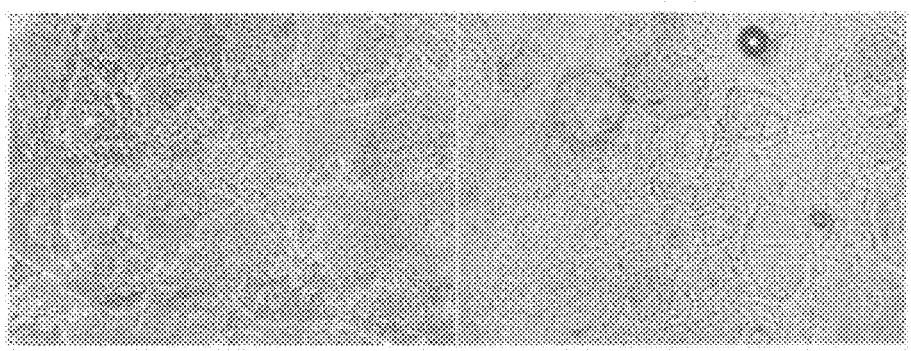

FIG. 26 a-b shows two micrographs of images of BPEI (SPS/PDAC) multilayer coatings fabricated onto agarose matrices.

Figure 27:
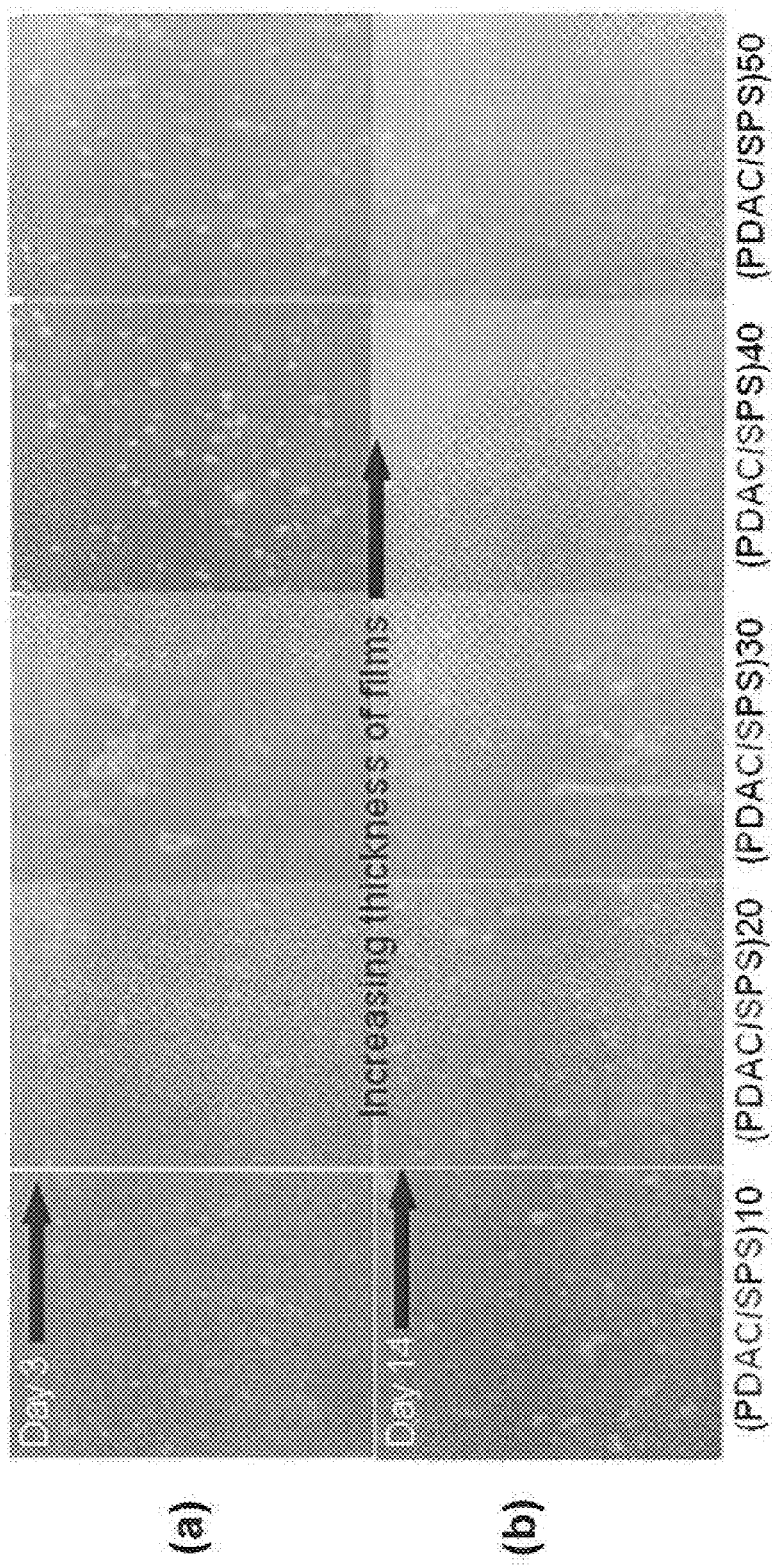

FIG. 27 a-b shows fibroblast adhesion behavior on (PDAC/SPS) multilayers on a plane glass substrate.

DETAILED DESCRIPTION OF THE INVENTION

The present disclosure is directed to an economic process for a template or scaffold that may be used in a variety of applications. The scaffold can achieve a highly ordered high-aspect ratio architecture useable in a variety of applications. The scaffolds contain conduits that can range from a diameter of 100 nm to a diameter of 1 mm. Solely by way of example, and not by way of limitation, a typical scaffold according to an embodiment of the present invention may have conduits with diameters ranging from 1 to 1000 microns, and more specifically from 50 to 300 microns.

In one application described herein, the structure may be used to provide a neurological scaffold to assist in the regeneration of nerve fibers in spinal cord injuries. In this application, the scaffold has the necessary biocompatibility to permit implantation at the site of the CNS injury. Furthermore, it can be manufactured in a way that permits the introduction of neurotrophic agent to promote nerve growth.

In another application, nano-scale structures provide a highly ordered nanowire or nanoconduit array. In this embodiment, extremely high aspect ratio structures can be economically achieved. The process described herein produces highly ordered arrays of cylindrical pores that can be greater than one millimeter in length with an aspect ratio (length/diameter) greater than ten. In practice, the process has been used to produce 200 µm diameter holes in excess of 3 mm in length (an aspect ratio >150). The structures described herein are constructed with polymer constituents that may be selectively removed. Common construction techniques used in fiber optic technology may be employed to produce elongated bare polymer fibers or clad polymer fibers.

In another application, scaling-up of the scaffolds is demonstrated for use in a broader range of clinical applications involving nerve repair. In this application, scaffolds are provided with channels up to and beyond 1 cm in length with face dimensions in the 1 cm$^2$ range.

In another application, scaffolds are provided that are particularly useful for the repair of peripheral nerves. In this application, a reservoir is incorporated into the construction of the scaffold from which growth factor diffuses across the agarose hydrogel walls in a time-release manner. This design allows for the prolonged and sustained axonal regeneration due to the continued presence of growth factor.

As will be described in greater detail herein, the selective removal of polymer fibers creates pores or apertures whose length, diameter, shape, and spatial arrangement can all be carefully controlled. Instead of using conventional techniques described above, the multi-component polymer fiber templates described herein utilize dissimilar polymers that are selectively dissolved in various solutions. There are several unique advantages to the process described herein. The chemistry involved does not generally expose the materials to aggressive chemical etchings or subject them to mechanical shear in tensile stresses that result from an extrusion process, as described above. The process does not involve mechanical or laser drilling, which are ineffective at the nano-scale. Furthermore, the process is effective with biocompatible components. Some standard manufacturing techniques, such as laser drilling, is not effective with biocompatible components, such as gels. Furthermore, the process described herein is cost effective.

Example One

Biocompatible Scaffold

Spinal cord injuries impact approximately 10,000 Americans each year, usually cause lifelong disability due to the inability of the central nervous system (CNS) to regenerate naturally. However, while a cure for this devastating condition remains elusive, the level of understanding of the primary and secondary responses involved in spinal cord injury continues to increase. Regeneration of axons through a lesion site has been shown in experiments, usually as the result of neurotrophins and/or support cells to the site of the injury. However, it is typically random and, therefore, the chance of functional reconnection is minimal. Consequently, potential strategies for effective regeneration are evolving, such as the use of a nerve guidance channel. The ideal nerve guidance channel must have several properties. First, it must be biocompatible, with degradation products that are neither toxic nor immunoreactive in the CNS environment, and degrade slowly enough to provide a physical scaffold for regeneration, but quickly enough to avoid any unpredictable long-term effects of having foreign substances in the body. Second, it must have appropriate adhesiveness and capable of hosting neurotrophic factors with transmembrane signaling properties to stimulate axonal growth. Third, it should guide regenerating axons physically via predefined pathways and/or chemically via neurotrophic factor gradients through the channel.

The process described herein permits fabrication of highly ordered monodisperse pores in extracellular matrices. The term "monodisperse" refers to the fact that the pores have uniform size. The ability to produce uniform pore size permits close-packing of pores and results in a high-porosity scaffold, which is desirable for nerve regeneration applications. In an exemplary embodiment, the pores are cylindrical and parallel with diameters that can range from tens of microns to hundreds of microns with lengths exceeding several millimeters. As will be described below, the templated extracellular matrix may be readily used to assist in axonal regeneration following spinal cord injury.

Figure 1:
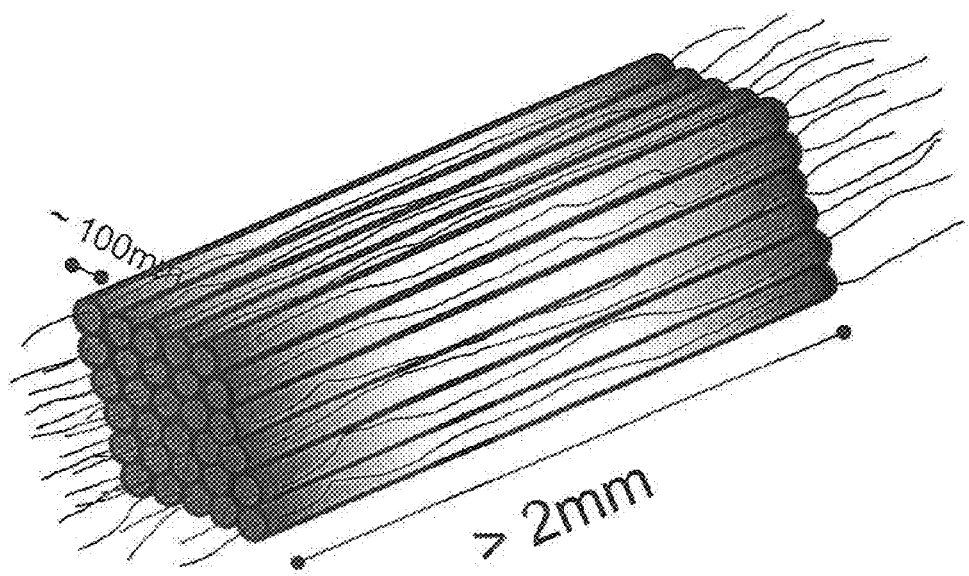
FIG. 1 is an enlarged perspective view of a biocompatible scaffold.
Figure 2:
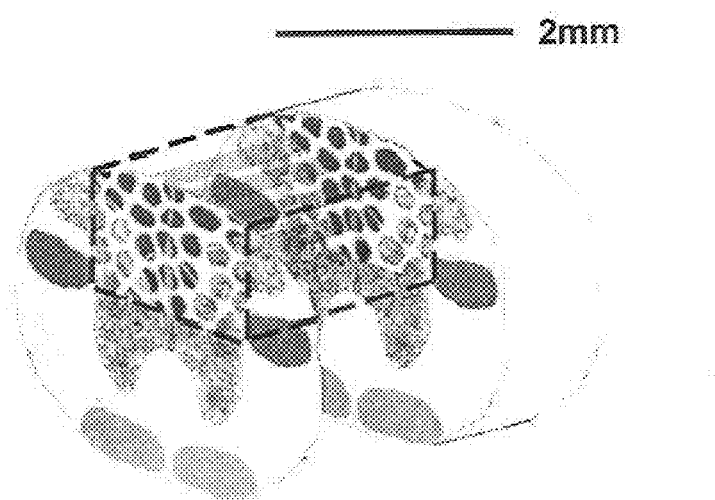
FIG. 2 illustrates implantation of the scaffold of FIG. 1 at the site of a spinal cord injury.
Figure 2:
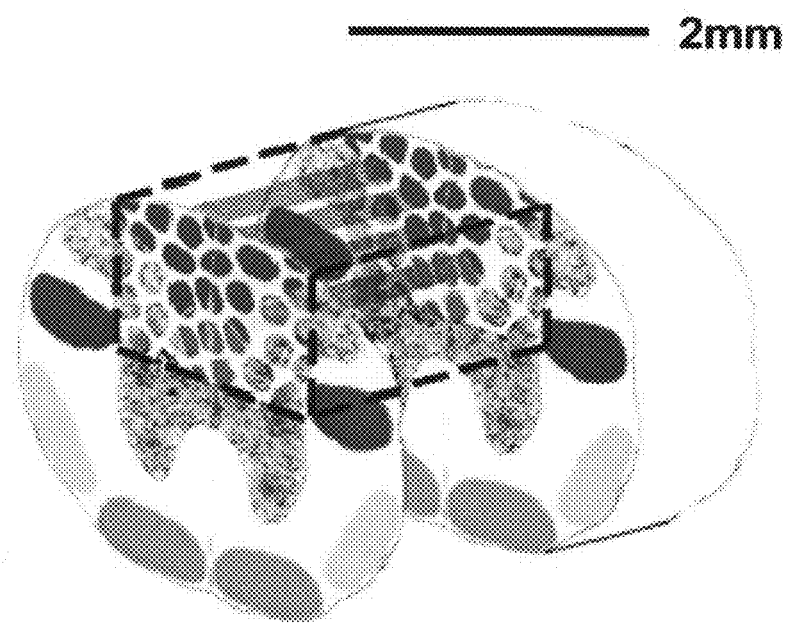

For applications in axonal regeneration, it is necessary to implant a biocompatible scaffold that directs the nerve growth in the desired orientation. FIG. 1 diagramatically illustrates a biocompatible nerve regeneration scaffold designed specifically for experiments aimed at repairing central nervous system injuries in rats. FIG. 2 illustrates the nerve regeneration scaffold positioned in the spinal column. In this particular application for nerve regeneration in rats, the scaffold should have close packed pores (>50% pore volume), exceed two millimeters in length, and have approximately 1 μm to >100 μm diameter conduits.

In experiments, it has been determined that a satisfactory scaffolding material can be manufactured from agarose, which is an inert polysaccharide. Agarose forms a stable helix structure upon thermal polymerization to thereby create a robust gel. Agarose is typically a liquid above 83° C. and forms a gel below 40° C. Those skilled in the art will appreciate that the biopolymer gels like agarose are mostly water. A typical gel may be 97% water. The process described herein is compatible with biopolymer gel processing.

To stimulate axonal regeneration, the scaffold must contain the appropriate neurotrophic factors at the time of implantation. Pores within the agarose gel may be filled with an extracellular matrix such as Matrigel® or Fibrin, which are capable of hosting nerve-growth stimulating molecules or cells such as Brain Derived Neurotrophins (BDNF) or Bone Marrow Stromal (MSC) cells. Other neurotrophic agents may be used in place of or in addition to BDNF or MSC cells.

Figure 3:
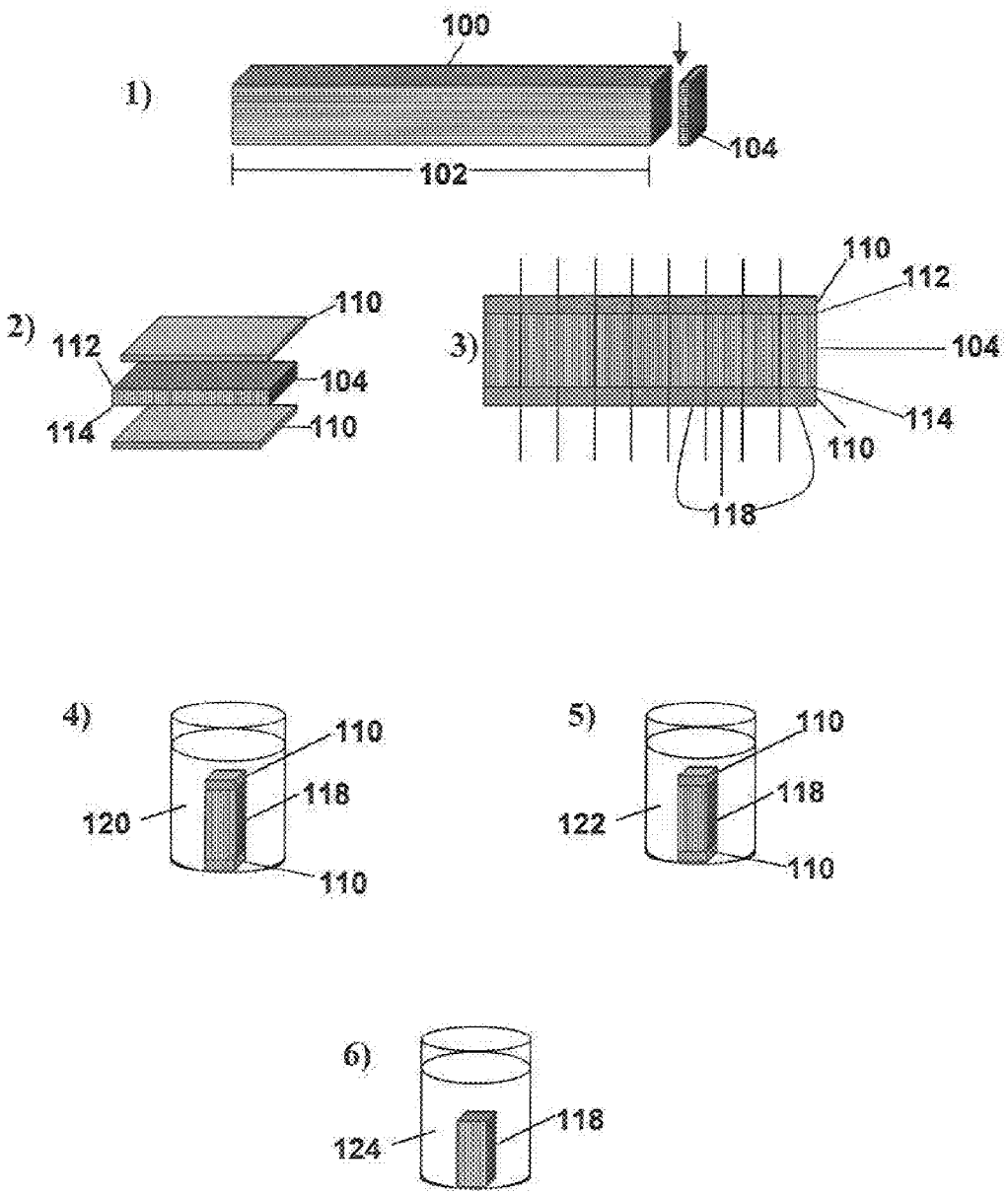
FIG. 3 illustrates a process used to create the biocompatible scaffold of FIG. 1.

The process of generating the agarose scaffold requires multiple steps, illustrated in FIG. 3. The first process involves the fabrication of a polymer fiber template. The fiber template illustrated at step one comprises two dissimilar polymer fibers. In one embodiment, polystyrene (PS) fibers are surrounded by a polymethylmethacrylate (PMMA) matrix. The PS fibers may be arranged in a desired spatial arrangement within the PMMA matrix. Other polymers can be satisfactorily used in place of the PMMA and/or the PS.

As discussed above, conventional techniques for optical fiber manufacturing may be employed. A fiber template may originally start with a large array of approximately one-half inch in diameter. The selected polymers have similar viscothermal characteristics. The fiber template is heated and lateral pressure applied to the sides of the large diameter bundle. The bundle may be drawn out under heat and pressure. Those skilled in the art will appreciate that as the fiber template bundle is drawn out, the diameter of the bundle and embedded PS fibers decreases. With this process, it is possible to achieve diameters for the PS fibers less than 100 nm.

At step one in FIG. 3, a fiber template 100 has been manufactured in accordance with the techniques described above so that the diameter of the embedded PS fibers equals the diameter of the desired pore size. The PS fibers are oriented along a longitudinal axis 102 of the fiber template 100. In the first step, a slice 104 of the fiber template 100 is cut to the desired length of the final product. For applications as a nerve regeneration scaffold, the fiber template slice 104 may be approximately 2 mm in length. In this application, a diamond saw may typically be used to cut the template to the desired length. Sanding or polishing of the cut surfaces is typically required to provide smooth working surfaces.

In step two, end caps 110 are chemically bonded to the face of the fiber template slice 104. In one embodiment, the end caps 110 are polystyrene sheets that will chemically bond with the PS fibers within the fiber template slice 104. An upper face 112 of the fiber template slice 104 is dipped in toluene/acetone and one end cap 110 chemically bonded to the upper face. The process is repeated by dipping a lower face 114 of the fiber template slice 104 in toluene/acetone and chemically bonding the second end cap 110 to the lower face.

The end caps 110 provide structural support and keep the PS fibers in place during the remaining manufacturing process. In addition, the PS end caps 110 serve to assure that the pores in the biocompatible scaffold remain open at the end of the processing.

In step three, the fiber template slice 104 and attached end caps 110 are cut into columns 118 that approximately the final desired dimension of the biocompatible scaffold.

Step four illustrates a single column 118 placed in a solution that selectively dissolves the PMMA fiber cladding leaving only the PS fibers and PS end caps 110 intact. Those skilled in the art will recognize that multiple columns may be processed in a single batch. Furthermore, although not illustrated in FIG. 4, a polymer side plate may be chemically bonded to the end caps 110 of the column 118 to provide additional structural support. The end caps 110 of multiple columns may be chemically bonded to a single side plate to simplify the production of multiple scaffolds.

In the embodiment discussed herein, the PMMA matrix is dissolved by placing the column 118 in a propylene carbonate bath 120 at 45° C. for approximately 24 hours. This process is repeated three separate times with fresh solvent to assure complete dissolution of the PMMA matrix. Although FIG. 1 illustrates the processing of only a single column 118 at step four, in practice, it has been shown that six template columns 118 may be processed in approximately 50 cc of the propylene carbonate bath 120 in the process described above. Following the removal of the PMMA matrix, a washing step may be used to remove any residual traces of the polypropylene carbonate solution.

Following the removal of the PMMA matrix, the column is placed in a permeate liquid biopolymer gel bath 122 at approximately 80° C., as illustrated in step five of FIG. 3. As noted above, agarose is a polysaccharide well suited for this application. At 80° C., the agarose is in liquid form and permeates throughout the PS fibers to form a biocompatible matrix surrounding the PS fibers. Ultrasound energy may also be applied to the bath 122 to provide uniform permeation and to eliminate possible bubbles in the agarose liquid. In an exemplary embodiment, the bath 122 is sealed to prevent contamination and placed in a water-sonicating bath (not shown) at approximately 90° C. for approximately 1-2 minutes.

After sonification, the bath 122 is removed from the water bath (not shown) and allowed to cool to room temperature. At room temperature, the agarose bath 122 forms a gel in approximately four hours.

In step six, excess agarose gel may be removed with a knife blade, scalpel, sander, or other suitable instrument. Following the removal of excess agarose, the column 118 is placed in a solution that selectively dissolves the PS fibers and the PS end caps 110 from the column 118.

As noted above, the PS end caps 110 serve to assure that the pores in the biocompatible scaffold remain open when the PS fibers are dissolved at the end of the process. Because the fiber template slice 104 is cut to the desired length at the start of the manufacturing process, there is no need to cut the column 118 after the pores have been removed by dissolving the PS fibers. Cutting to length after the pores have been formed could lead to a collapse of the walls. The chemical processing to form pores of the desired length avoids mechanical damage that may occur with other technologies.

In an exemplary embodiment, the PS fibers and PS end caps are dissolved by placing the column 118 in a tetrahydrofuran bath 124 at room temperature for approximately 24 hours. This process is repeated approximately three times. As noted above, batch processing of columns is possible. It has been determined that approximately 50 cc of tetrahydrofuran is sufficient to dissolve the PS fibers and PS end caps 110 for approximately six columns. At the end of this process, only the agarose scaffold remains. The PS fibers that extended through the agarose gel are dissolved in the tetrahydrofuran bath 124 to create an array of pores in the agarose scaffold. The pores have the diameter and physical arrangement of the PS fibers and extend through the length of the column 118.

Figure 4:
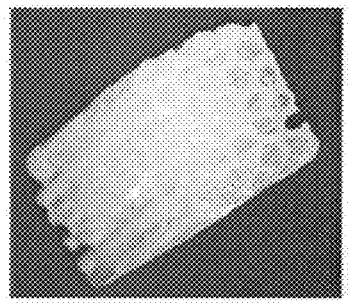
FIG. 4 is a photograph of a sample of the biocompatible scaffold of FIG. 1.
Figure 5A:
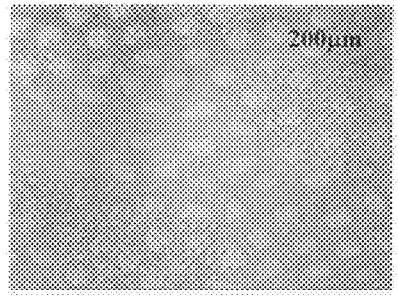
FIGS. 5A-5E illustrate an alternative embodiment of a biocompatible scaffold and demonstrate uniform pore structure.
Figure 5B:
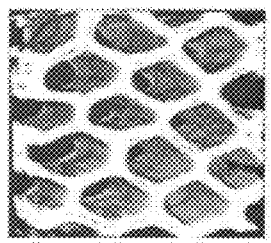
Figure 5C:
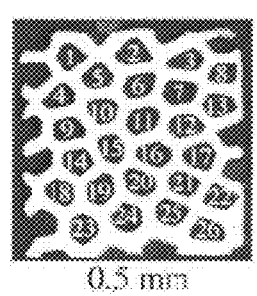
Figure 5D:
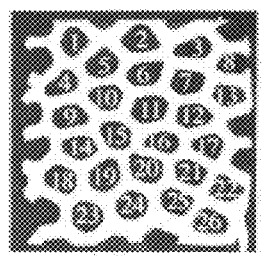
Figure 5E:
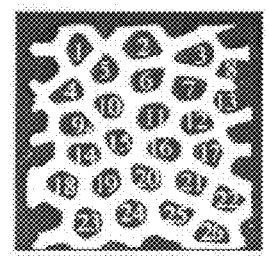

In the photo shown in FIG. 4, the nerve regeneration scaffold has approximately 200 µm pore size and approximately 100 µm wall thickness. In the embodiment illustrated in FIG. 4, the nano-scale structure has a porosity of approximately 44 percent and has a substantially circular cross-section. In a subsequent design, illustrated in FIG. 5A, the scaffold has approximately 200 µm pore size, 33 µm wall thickness, to achieve a porosity of approximately 60 percent. The wall thickness in the described process enables the high pore volume. FIG. 5A illustrates the scaffold with the fibers still in place. FIG. 5B illustrates the scaffold of FIG. 5A following the removal of the polymer fibers leaving a honey-comb pore arrangement with pores. A three dimensional (3-D) reconstruction reveals substantially uniform pore structure from end to end. FIGS. 5C-5E are cross-sections of the scaffold at various depths. In these images, individuals pores have been numbered so that changes in structure may be detected.

FIGS. 6-8 are photographs of slides illustrating nerve growth using the biocompatible scaffold. In an exemplary embodiment, the pores may be filled with a nerve growth factor, brain derived neurotrophic factor (BDNF), as noted above. In other embodiments, the scaffold pores may be filled with genetically engineered marrow stromal cells (MSC) that secrete brain derived neurotrophic factor (BDNF). For experimental purposes, the MSC may also be engineered to express a green fluorescent protein (GFP) reporter gene. Those skilled in the art will appreciate that GFP fluoresces under a microscope with an appropriate light source, allowing identification of modified cells that have been implanted within the scaffold.

A rat model of spinal cord injury was used to test the ability of scaffolds to stimulate and guide axonal regeneration in vivo. Spinal cord lesions were created by aspirating tissue at the C3 vertebra level (resulting in a cavity matching the dimensions of the scaffold: 2 mm long, 1.5 mm wide, and 1.4 mm deep) and subjects were divided into three groups. The first group was treated with unfilled scaffolds, a second group was treated with scaffolds filled with a non-BDNF secreting MSCs (GFP-MSCs) and a third group was treated with scaffolds filled with BDNF secreting MSC (BDNF-GFP-MSCs). Thirty days after implantation, the rats were perfused with paraformaldehyde and the spinal cords were sectioned in the sagittal plane.

The images in FIGS. 6-8 have different magnifications. A scale bar in each image equals 200 µm. FIG. 6A illustrates nerve growth using the group with empty scaffolds. FIG. 6B illustrates the results with scaffolds with the non-BDNF secreting MSC (GFP-MSC). FIG. 6C illustrates results with scaffolds filled with BDNF secreting MSC (BDNF-GFP-MSC). A comparison of FIGS. 6A-6C indicates that the scaffolding alone (FIG. 6A) provides some basis for axonal growth while the introduction of neurotrophic agents (FIG. 6C) promotes a significant increase in nerve growth.

FIGS. 6A-6C illustrate nerve growth in a single channel of the nerve regeneration scaffold. FIG. 7 illustrates nerve growth in multiple channels of the nerve regeneration scaffold. This demonstrates the effectiveness of the multi-lumen nerve growth scaffold for promoting and directing nerve regeneration.

Additional experiments were conducted to demonstrate the value of the scaffold to assist in the development of functional nerve growth. In FIG. 8A, immunolabeling against GFP is used to highlight implanted BDNF-secreting MSCs, while in FIG. 8B immunolabeling against Neurofilament (NF), a general axonal marker, is used to highlight axon growth. The images on the left in FIGS. 8A-B were taken from animals which received BDNF-secreting MSCs within a scaffold, while the images on the right in FIGS. 8A-B were taken from animals which received BDNF-secreting MSCs without a scaffold. Although both images demonstrate nerve growth, the nerve growth utilizing the scaffold is highly linear and organized while the non scaffold nerve growth is somewhat random in nature.

For a successful nerve regeneration scaffold, vascularization is necessary to both promote and sustain axonal growth. FIG. 9 illustrates evidence of vascular regeneration within implanted scaffolds. A scale bar in the image equals 100 µm. FIG. 9 shows multiple channels in the nerve regeneration scaffold and the areas indicated by the arrows show vascular growth within those channels.

Figure 10:
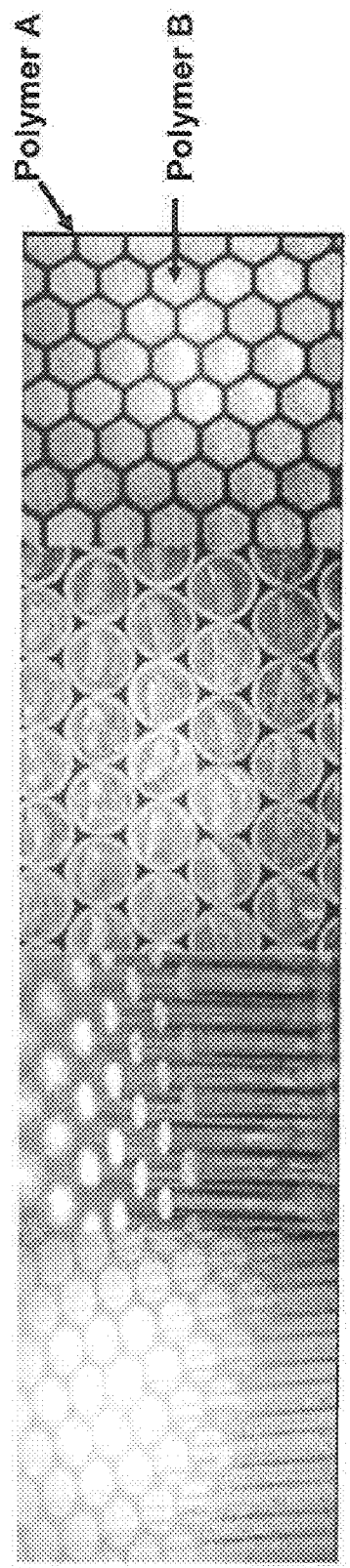
FIG. 10 illustrates alternative embodiments of cross-sectional areas of the biocompatible scaffold of FIG. 1.

The scaffold illustrated in FIGS. 1-4 have pores with a generally circular cross-section. However, those skilled in the art will appreciate that other cross-section shapes may also be readily produced. FIGS. 5A-5E illustrate a honey-comb cross-section. FIG. 10 illustrates circular cross-section and hexagon cross-section designs. Other shapes, such as rectangles, squares, or irregular shapes are also possible. The present invention is not limited by the specific cross section of the shape of the pores.

Example Two

Ordered Array Nanodevice

The biocompatible scaffold described above has pore size diameter in the 10 µm-200 µm diameter range. However, with the application of the principles described herein, pore size can be reduced to a much greater degree, depending on the application. Experiments have shown that pore size may be reduced to <10 nm in diameter. The nanoscale template may also have bio-applications, such as the nerve repair process described above. Furthermore, at this scale, other applications are possible, as will be described in greater detail below.

A multi-component polymer fiber template may be used to enable the selective deposition of dissimilar materials into well defined arrays of nanoconduits or nanoconductors having specific arrangements or configurations. This structure permits applications, such as thermoelectric devices, or semiconductor-based devices. In these applications, positive and negative conducting elements may be manufactured in the nano-scale device.

In the process described below, a nanowire based thermoelectric device is manufactured. In FIGS. 1-5, polystyrene fibers were embedded in an ordered array within a PMMA matrix. The bi-component polymer process of FIGS. 1-5 can be extended to multi-component polymer fibers. In one example of this application, two different polymer fibers are embedded within a PMMA matrix. In an exemplary embodiment, PS fibers and polyvinyl alcohol (PVA) polymer fibers are arranged in a desired ordered array in a PMMA matrix. As described above with respect to step one in FIG. 3, the ordered array may initially have a large diameter and, through the application of heat and pressure, be drawn out until the PS and PVA fibers have the desired diameter.

Figure 11:
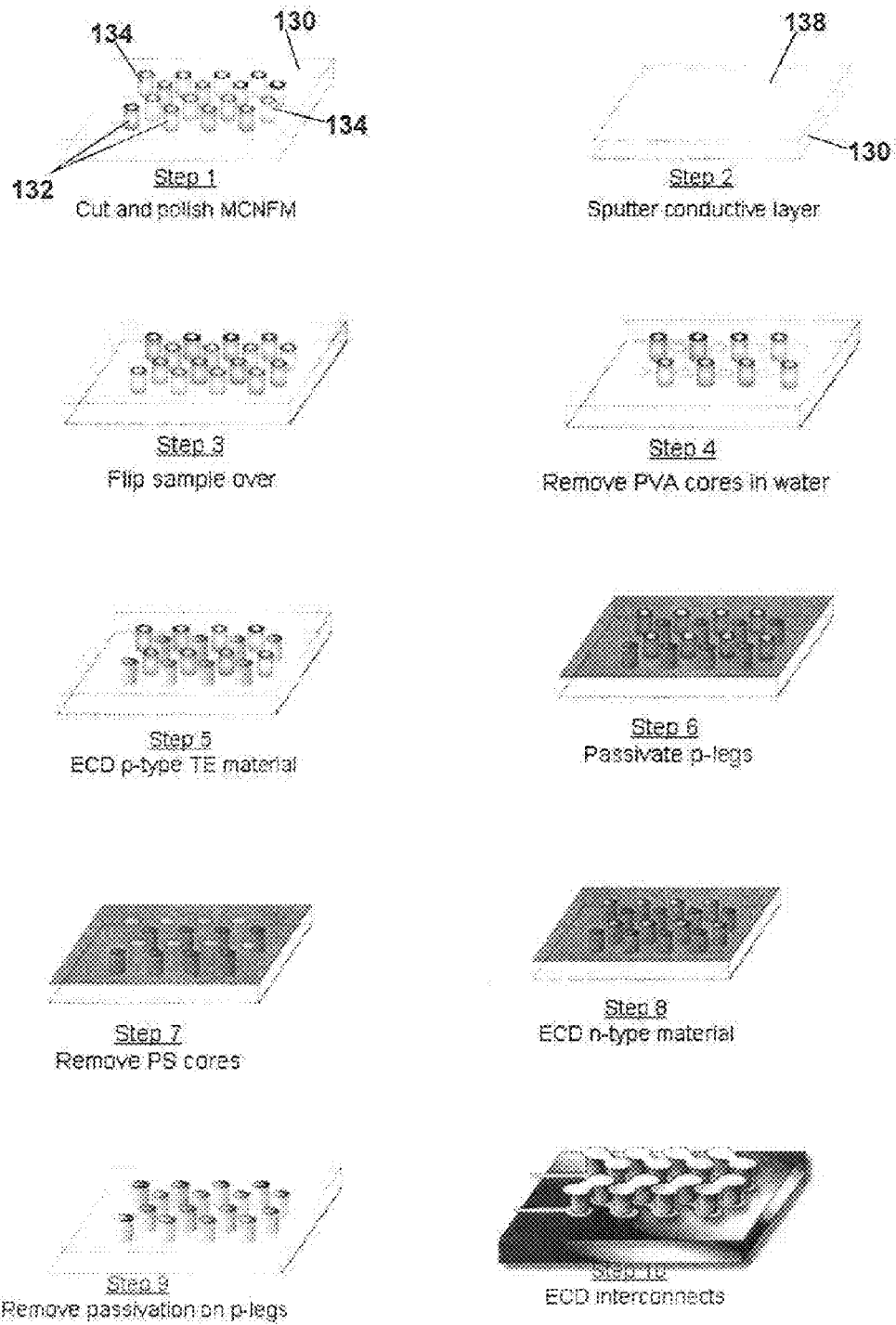
FIG. 11 illustrates a process for creating a nano-scale structure.

In step one, shown in FIG. 11, a slice of a multi-component nano fiber matrix (MCNFM) 130 is cut and polished. As previously discussed, a diamond saw may be suitable for cutting a slice having the desired pore length. The MCNFM slice 130 differs from the fiber template slice 104 (see FIG. 3) in that it contains two dissimilar polymer fibers contained within the PMMA matrix. In the example illustrated in FIG. 11, the MCNFM slice 130 comprises an ordered array of PVA fibers 132 and PS fibers 134.

At step two, the surface of the polished MCNFM slice 130 is covered with a conductive layer 138. Conventional techniques, such as sputtering, can be used to apply the conductive layer 138 to the MCNFM slice 130.

In step three, the sample is flipped over to better illustrate the reaming process steps. However, this step is not required in practice because the subsequent steps of dissolving fiber cores will occur irrespective of the orientation of the MCNFM slice 130

In step four, the MCNFM slice 130 is placed in water. Those skilled in the art will appreciate that PMMA polymer and PS polymer do not dissolve in water. However, the PVA fibers are soluble in water and are therefore removed in step four. The selective removal of the PVA fibers 132 leaves an ordered array of pores in the MCNFM slice 130 in place of the PVA fibers.

In step five, a thermoelectric material is deposited in the pores created in step four. That is, a thermoelectric material is deposited within the pores created by the removal of the PVA fibers 132. In an exemplary embodiment, electrochemical deposition (ECD) is used to deposit a p-type thermoelectric material in the pores created by the removal of the PVA fibers 132.

In step six, a passivation layer is added to passivate the p-type material to protect it in subsequent processing steps. This process is well known in the art and need not be described in greater detail herein.

In step seven, the MCNFM slice 130 is placed in a second solution to dissolve the PS fibers 134. In an exemplary embodiment, the MCNFM slice 130 may be placed in a solution of tetrahydrofuran bath to remove the PS fibers 134. Those skilled in the art will appreciate that PMMA and PVA are insoluble in tetrahydrofuran. Thus, steps 4 and 7 could be reversed. That is, the MCNFM slice 130 could have been placed in the tetrahydrofuran bath in step 4 to dissolve the PS fibers 134 rather than the PVA fibers 132.

In step eight, the pores created by the removal of the PS fibers 134 are filled with a semiconducting material. In an exemplary embodiment, an ECD process is used to deposit n-type thermoelectric material in the pores created by the removal of the PS fibers 134 in step seven.

In step nine, the passivation layer over the p-type material is removed and, in step ten, an ECD process may be used to deposit interconnecting conductors between the p-type material and n-type material to create the desired electrical array. Thus, the multi-component process illustrated in FIG. 11 may be created with a long pore length and high aspect ratio architecture that cannot be achieved by conventional processes Depending on the application, the matrix surrounding the PVA fibers 132 and PS fibers 134 can be removed or left intact. If the matrix is left intact, a polymer matrix, such as PMMA, may be replaced by a different matrix structure having the desired similar viscothermal characteristics that allow processing to generate the basic MCNFM material, as described above.

In the example described in FIG. 11, the matrix comprises PMMA. It is known that PMMA has low thermal conductivity. In applications where heat generation is not an issue, the PMMA matrix may be left intact to provide increased structural integrity. In applications where heat dissipation is desirable, an additional step (step 11) can be added to place the device in a final bath to dissolve the surrounding matrix. If the matrix is PMMA, a propylene carbonate bath may be used.

Figure 12:
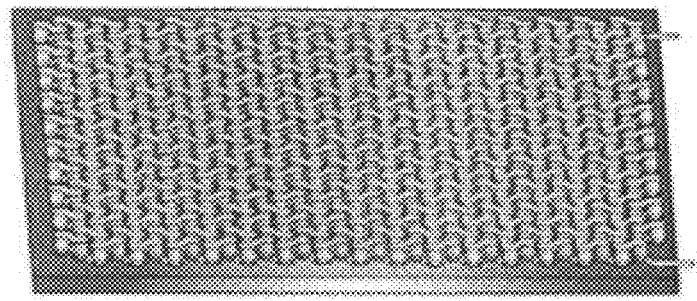
FIG. 12 illustrates a highly ordered array of nano-scale conductors created using the process of FIG. 11.

FIG. 12 illustrates a finished product in which a large ordered array of nanoconduits have been processed (e.g., filled with semiconducting material) and interconnected with conductive elements.

Those skilled in the art will appreciate that the process described in FIG. 11 may be altered. For example, the removal of PVA fibers 132 and PS fibers 134 may be reversed as described above (i.e., reverse steps 4 and 7). Alternatively, PMMA maybe used for the core fibers and placed in a matrix of, by way of example, polystyrene. Thus, the specific polymers utilized for the various components illustrated in FIG. 9 maybe interchanged. Furthermore, the deposition of p-type material in the pores created by the removal of PVA fibers 134 could be substituted with n-type material in step five. In this embodiment, step eight would involve the deposition of p-type material. Thus, those skilled in the art will appreciate that the exemplary embodiment of FIG. 11 may be readily altered. The present invention is not limited by the specific fibers or the specific sequence of steps described herein.

Other variations are also possible. For example, the PVA fibers 132 and PS fibers 134 are all the same diameter in FIG. 11 resulting in uniform pore diameter. However, the original MCNFM slice 130 may contain fibers of different diameters. For example, in one system architecture it may desirable to interconnect a number of the pores filled with semiconductor material to a common conductor. To reduce current density through the common conductor, it may have a larger diameter polymer fiber at step 1 of the process resulting in a larger diameter pore upon completion of the process.

In another example, it is known that the heat flux and current density in N-type material is different from the heat flux and current density in P-type material. Using the process described herein, it is possible to adjust the diameter of the PVA fibers 132 or the PS fibers 134 to compensate for the differences in heat flux and current density. In this example, all the PVA fibers 132 have the same diameter and all the PS fibers 134 have the same diameter, but the diameter of the PVA fibers is different from the diameter of the PS fibers. Those skilled in the art will appreciate other configurations requiring pores of different diameter may also be readily implemented using the techniques described herein.

In yet another alternative embodiment, the multi-component process of FIG. 11 may be replaced with the bi-component process described in FIGS. 1-5. That is, a large area matrix may be embedded with a single type of polymer fiber to create a large ordered array of pores for other applications.

Figure 13:
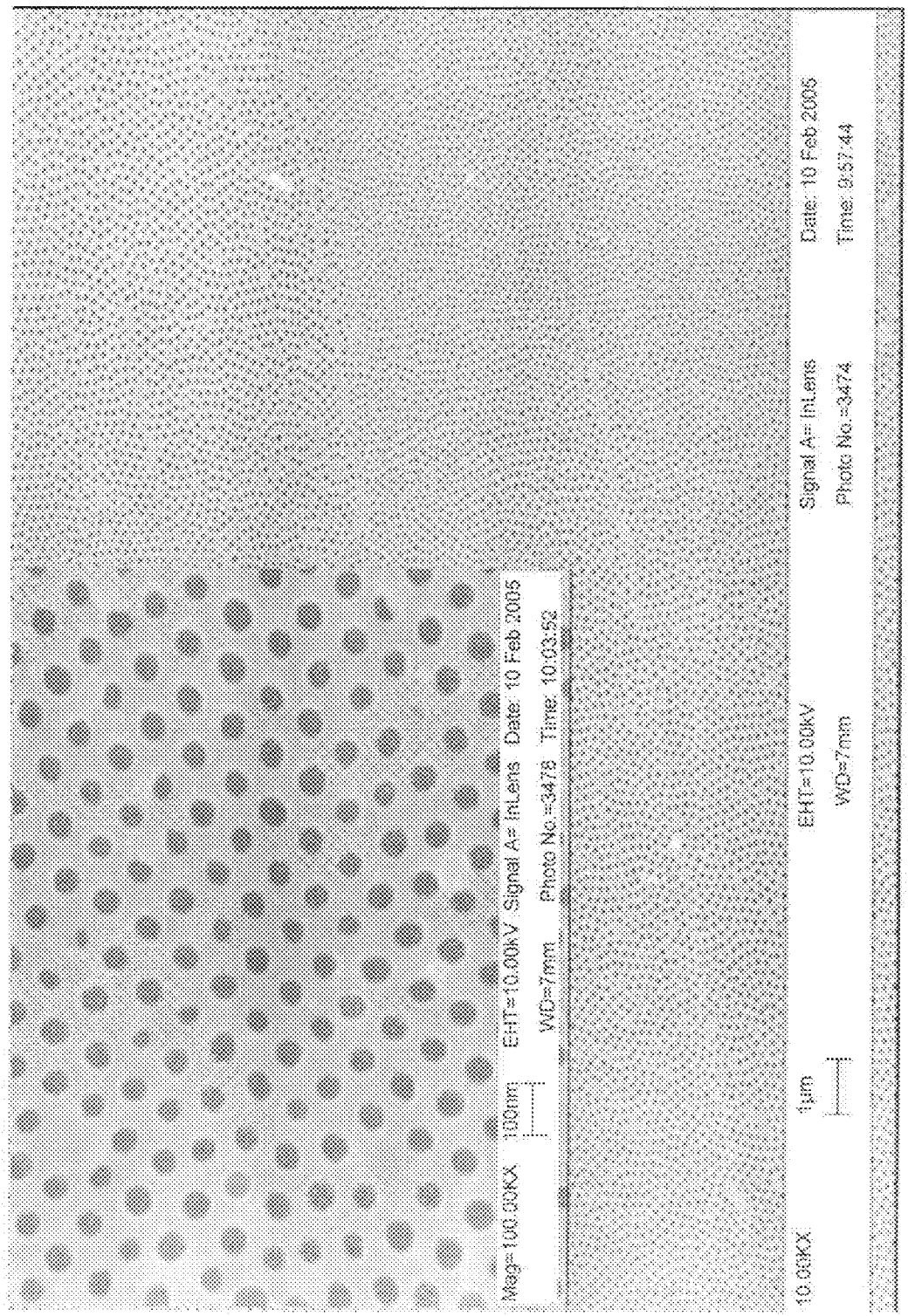
FIG. 13 are photographs of a magnified nanopore array.

FIG. 13 illustrates a highly magnified (10,000×) image of nanopores in a polymer matrix. The nanopores were produced with a process similar to that illustrated in FIG. 11, but with a plurality of only one type of polymer fiber embedded in a second polymer matrix. For example, PVA fibers may be embedded in a PMMA matrix in step 1 shown in FIG. 11. The PVA fibers may be dissolved to create the desired nanopore arrangement of FIG. 13 simply by placing the matrix in water to dissolve the PVA fibers. The inset in FIG. 13 provides greater magnification (100,000×) to better illustrate the ordered array of pores.

In this embodiment, a number of applications are possible. For example, the nanopore array may be used as a filter. One surface of the nanopore array can be placed in contact with fluid, which passes through the pores, and thus filters based on pore size.

In an exemplary embodiment, the nanopore filter may be used to filter water. In one embodiment, the pores may be embedded or coated with an antibacterial agent. For example, silver has known antibacterial qualities. Silver or a silver compound could be embedded or coated along the length of the nanopores at a concentration sufficient to provide the desired antibacterial effect.

In yet another application, the nanopore structure of FIG. 13 could be used as conduits for electrical devices, such as nanowires or the like. It is possible to achieve a density of approximately $1 \times 10^{11}$ pores per square centimeter. This potentially provides a large, high-density conductor array.

As discussed above, a number of different polymers have been satisfactorily employed in the processes described herein. Table 1 below provides a partial list of polymers and associated solvents. Those skilled in the art will appreciate that other polymers may be employed in the manner described above.

TABLE 1

| Polymer/Solvent Pairs | |
| --- | --- |
| Polymer | Solvent |
| Polymethylmethacrylate | Propylene carbonate |
| Polystyrene | Tetrahydrofuran |
| Polyvinyl Alcohol | Water |

Example 3

Scalability of the Scaffolds

In other embodiments described herein, it has been demonstrated that scaffolds with channels 2 millimeters long could promote and guide axonal regeneration through the entire length of the scaffold. The present embodiment involves scaling the technology to dimensions with a broader range of clinical applications, which involve axonal regeneration and guidance up to and beyond 1 cm long with face dimensions (the scaffold plane perpendicular to the longitudinal axis of the channels) up to and beyond the 1 cm² range. The scaffolds of the present embodiment were fabricated following the same procedures as in Example 1, above, with the primary exception of the template dimensions. The previous embodiments used Multicomponent Fiber Bundles (MCFBs) with 200 micron diameter fiber cores separated by 100 micron thick walls in a hexagonal packed arrangement. The templates/scaffolds of the present embodiment have face dimensions exceeding 1 cm² with channels up to 1 cm in length. A variety of nerve guidance scaffold channel diameters and wall thicknesses are reported to further demonstrate the range of dimensions possible with this technology.

Multi-component Fiber Bundles (MCFB) were fabricated by Paradigm Optics Inc. and consisted of various diameter Polystyrene (PS) cores surrounded by a continuous matrix of Polymethylmethacrylate (PMMA). The solvent used to selectively etch the various fiber bundle constituents was purchased from Alfa Aesar and the PS endcaps attached to the fiber bundles were cut from polystyrene boxes purchased from VWR. Scaffolds were fabricated using distilled water and agarose from Sigma.

The MCFB used to fabricate nerve guidance scaffolds consisted of PS fiber cores surrounded by a continuous matrix of PMMA with a typical, as received length of 10 cm in the longitudinal direction. Typical MCFB cross sections were rectangular, in the range of 4-6 mm along one edge and 12 mm to 18 mm on another with the exception of the 40 micron wall/280 micron PS fiber core MCFB, which measured 20 mm by 20 mm. The range of PS fiber core diameters and spacing between cores is listed in Table 1.

TABLE 1

| PS fiber core diameters and spacing between cores | | | | |
| --- | --- | --- | --- | --- |
| Sample | Wall (μm) | Channel (μm) | Cross Section (mm × mm) | Length (mm) |
| 100/200 | 100 | 200 | 4 × 5 rectangle | 7.5 |
| 50/150 | 50 | 150 | 6 × 6 square | 7.5 |
| 40/280 | 40 | 280 | 10 × 10 square | 7.5 |

The MCFBs were cut with a diamond saw to the desired length, finished with 600 grit sand paper, and rinsed with ethanol. PS sheets with dimensions matching the MCFB template were cut from 1.0 mm thick sheets of PS and bonded to the ends of the MCFB. Bonding was achieved by immersing the PS sheets in Cyclohexane (Alfa Aesar) at 45 C for 10 seconds and quickly pressed on the ends of the MCFB. PS rectangles were bonded to each of the MCFB ends this way. Cyclohexane was specifically selected to selectively and partially dissolve only the PS fibers and the PS rectangles so that the PMMA matrix remained intact. The same process was used to bond PS side supports spanning from PS end cap to PS end cap (end caps refer to the previously mentioned PS rectangles), which give the templates rigidity in the latter steps of processing. The template assemblies are then immersed in a propylene carbonate (PC)/acetonitrile (ACN) 80/20 vol/vol % solvent bath at 45 C and stirred with a magnetic stir bar for 24 hours (repeated 3 times). The addition of 20 vol % ACN increased the solubility of PMMA enough to achieve reasonable etch rates to allow etching templates that were significantly larger compared to the other embodiments. Adding more the 20 vol % ACN was deleterious in that PS components began dissolving along with the PMMA. Approximately 100 ml of etch bath is used for 1 cc of template. Since PS is not soluble in the PC/ACN etch bath the PMMA matrix is selectively removed leaving only the PS fibers, end caps and side supports intact. Once the PMMA is removed the fiber template is rinsed in distilled water three times (approximately 100 ml ethanol for each ml of template) for 15 minute each wash. The fiber templates are then immersed in a 3.0% wt. % agarose hydrogel 97% wt. % distilled water solution at 80 C, immediately followed by one minute of centrifugation at 5000 rotations per minute for one minute, and allowed to cool to room temperature (centrifugation facilitates agarose hydrogel gel permeation through the template). The incorporation of a centrifugation step assures complete permeation of the liquid agarose hydrogel through the template. Selective removal of all the PS template components (fibers and endcaps) is achieved by immersing the agarose hydrogel permeated template in a tetrahydrofuran (THF Alfa Aesar) bath at room temperature for 24 hours (approximately 100 ml THF to each ml of template). The agarose hydrogel scaffolds were then rinsed in an acetone bath to remove residual PS followed by a final immersion and storage in distilled water.

Scaffold microstructural analysis was conducted to characterize features such as channel and wall dimensions, calculate channel volume percentage per unit volume scaffold and channel/wall integrity and uniformity along the longitudinal axis. Scaffolds were mounted in low gelling point agarose hydrogel (low molecular weight agarose hydrogel Sigma Aldrich #7067). To improve contrast for optical imaging, 0.02 vol % Single-wall carbon nanotubes are incorporated into the agarose hydrogel scaffolds during the agarose hydrogel casting step. Scaffolds were immersed in 3 wt % low molecular weight agarose hydrogel solutions at 60 C for 1 minute and centrifuged at 5000 rpm for 1 minute. In this case, centrifugation permeated the low molecular weight agarose hydrogel through the scaffold channels. After cooling and gelation, the mounted scaffolds were rigid enough to withstand mechanical grinding or sanding. Grinding down to various depths along the longitudinal axis of the scaffolds was achieved using coarse sand paper (240 grit) and polished using fine (1200 grit) sandpaper. Optical microscopy was conducted using a Zeiss microscope illuminating the back side of the mounted scaffolds using fluorescent white light.

The theoretical channel area (or channel volume per unit volume of scaffold) was calculated based on the close-packed hard cylinder model. The diagonal of the unit cell of a close-packed array is referred to as the close-packed direction, hence the spacing between cylinders is determined by the surrounding cladding or wall thickness. The channel volume percent per unit volume of scaffold was measured using histograms, which typically included 1 square millimeter area and approximately 100 to 200 channels.

The present embodiment thus involves the fabrication of scaffolds to enable bridging through the damaged tissue and reestablish nerve continuity. Precise control of scaffold channel size is enabled, allowing for separation between channels and the maintainance of a high degree of ordering in the range of millimeters to centimeters both perpendicular and parallel to the direction of axon growth. The scaffolds are designed and fabricated such that axon growth is consistent with the native nervous system environment with regard to relative position and density. The approach involves a patterning process that uses wet chemical etching to selectively remove polymer optical fibers while leaving the permissive axonal growth substrate (agarose hydrogel) intact.

Increasing the scaffold dimensions from 1.5 by 1.5 by 2 mm long in previously described embodiments to up to 1 cm by 1 cm by 1 cm long did require some modifications. As the dimensions perpendicular to longitudinal length increase beyond 5 mm, it becomes increasingly difficult to selectively remove the PMMA cladding at the center of the templates. This was mitigated by adding Acetonitrile (ACN) to the Propylene carbonate etch bath. ACN alone is too aggressive and would etch the PS fibers along with the PMMA cladding, hence only 20% vol % (enough to increase PMMA solubility, but not enough to increase solubility with the PS fibers) was added to increase solubility with PMMA to allow its complete removal. A related issue involved permeating the molten agarose hydrogel through the templates again as the dimensions perpendicular to the longitudinal direction increased to approximately 5 mm. Permeating the molten agarose hydrogel through the larger templates was accomplished by centrifuging the fiber templates while immersed in molten agarose hydrogel (80 C at 5000 rpm for 1 minute).

Images of the scaffolds listed in Table 1 detail the scaffold micro-structures at various depths along their respective longitudinal axes at low and high magnification. For example, micrographs in FIGS. 14 a,c and e represent the low magnification cross sections at 2, 3.75 and 5.5 mm, respectively, referenced from one end of the scaffold. Similarly, FIGS. 14 b, d and f represent higher magnification images at 2, 3.75 and 5 mm, respectively. The ordering in all the scaffolds is quasi-hexagonal in that the fiber templates used are slightly distorted during the fusing process (which results in a higher packing density as described below). The walls and channels of the scaffolds are within ~1% of the fiber template dimensions, thus indicating that the scaffolds form precise replicates of the original PMMA matrix in the original un-etched templates. It is also important to note that the order and dimensional tolerance of the walls and channels are maintained throughout the entire cross section of all the scaffolds shown in FIG. 14-16. There was concern that the inherently weak agarose hydrogel material would not withstand the rigors of processing as the scaffold walls decreased below 100 microns However, the 50 micron walls in the 50/150 and 40 micron walls in the 40/280 scaffolds are intact and maintain their integrity throughout the entire cross section of their respective scaffolds. The white boxes in the FIG. 15 highlight a cluster of 4 channels with a square arrangement (slight interruption in the hexagonal ordering due to slight distortion of the fiber cores as noted above). The higher magnification images in the right column (FIGS. 15 b, d and f) trace the continuity of the channels through the length of the scaffold, thus indicating that the channels are open from end to end. Likewise, the walls in this cluster maintain their dimensional tolerance, thus indicating that the scaffold maintains its mechanical integrity along the length of the scaffold as well. The same is true for the 100/200 and 40/280 scaffolds.

As discussed above, the channel volume per unit volume of the scaffold increases as the channel diameter/wall thickness increases. A maximum of 74% channel volume is reached when the wall thickness is zero as predicted by the hexagonal packed hard cylinder model. The channel per unit volume (or area) is plotted against the channel/wall ratio in FIG. 17. The solid black line represents the theoretical values for the hard sphere model. Interestingly, all of the scaffold channel porosities exceed the predicted values and this is attributed to the distortion mentioned above. The 100/200, 50/150 and 40/280 scaffolds have channel porosities of 42, 52 and 70 percent. These values are significantly higher than what has been reported in literature where 35 vol % has been the highest value achieved. The % channel volume is a key value in that the higher the value the greater the likelihood of restoring the native nerve networks.

A 1 $cm^3$ scaffold was fabricated to demonstrate that all dimensions can be scaled significantly compared to previous work. The scaffold was fabricated using at 40/280 template. As with the other similar scaffolds, this scaffold has the high degree of ordering and uniform channel/wall dimensions over the entire scaffold cross-section.

Example 4

Time-Release Scaffold

In another embodiment, the construction of time-release scaffolds for the repair of peripheral nerves is demonstrated. In order to sustain the growth of axons in peripheral nerves, adequate growth factor must be present. Thus, we have developed a novel scaffold design that incorporates a reservoir within the walls of the scaffold to sustain delivery of nerve growth factor.

Time-release scaffolds according to this embodiment are shown in FIG. 18. The top portion of the figure illustrates how the scaffold is ultimately to be surgically attached to the severed ends of a peripheral nerve injury. The middle portion of the figure is a schematic that illustrates the details of the concept. There are three essential features: 1) the open-ended sleeves enable attachment to the severed peripheral nerves, 2) the templated hexagonal array of nerve guidance channels, and 3) the growth factor reservoir integrated into the outer wall of the scaffold. The bottom portion of the figure illustrates the cross section at mid span perpendicular to the longitudinal axis. At the center of the scaffold cross section, the channels guide the nerves. Growth factor delivery from the reservoir to channels is controlled by diffusion through the agarose hydrogel walls. It is important to note that the entire scaffold is comprised of agarose hydrogel and as such there are no discontinuities between the channels and the reservoir other than the continuous, intrinsic pore network of the agarose hydrogel.

An example of the time-release reservoir scaffold design is shown in FIG. 19. It is an all agarose hydrogel scaffold with the open-ended sleeves and a close packed array of channels (100 wall/200 channel dimensions). In a separate experiment, polystyrene coupons (that would mock the templates used to pattern the reservoirs) were suspended in molten agarose hydrogel such that the coupons were completely encapsulated with agarose hydrogel upon cooling. Upon cooling and solidification, the agarose hydrogel/polystyrene coupon was immersed in tetrahydrofuran (THF). The THF permeated the interconnected pore network intrinsic to the agarose hydrogel, and completely dissolved the polystyrene coupon leaving a reservoir in its place.

The reservoir was integrated around the templated channel network through the use of a cylindrically-shaped mold. The cylindrical mold was designed such that the polystyrene fiber template was centered in the middle of the longitudinal axis. Molten agarose was cast into the mold such that it permeated the polystyrene fiber network and the cylindrical mold. Upon cooling, the assembly was immersed in THF to selectively etch the polystyrene fibers. All subsequent steps were as described for other embodiments disclosed herein. The inner diameter of the cylindrical mold was approximately 4-8 millimeters in diameter such that the agarose hydrogel surrounding the templated region was in the 2-3 mm range.

In all of the scaffold embodiments described herein, two issues to be aware of are the long-term fracture resistance of the scaffold and the interface between the scaffold and the host's tissue. Scaffold fracture can occur due to shear and tensile forces imposed by nearby muscle movements or impacts to the surface of the host's skin. The characteristics of the interface between the tissue to be regenerated and the scaffold must also be considered. A severed nerve cannot be stitched directly to the scaffold due to the relatively brittle nature of agarose. Adhesives and glues cannot be used due to the practical problem of blocking channels in the scaffold and because any application such materials directly to the scaffold can cause fracture. To address these issues, a biocompatible reinforcing tube can be used on the outside of the templated agarose scaffold as shown in FIG. 21.

"The surgical and medical product sold under the trademark TYGON® tubing, such as TYGON® S-50-HL and S-54-HL medical tubing, is a biocompatible material made of polyvinyl chloride (PVC) thermoplastic polymer with appropriate mechanical properties to serve as the outer reinforcing tube. Additionally, if sutures are needed, the TYGON® (polyvinyl chloride thermoplastic polymer) tubing can be sutured. If a medical grade crazy glue is used for anchoring, its texture is coarse enough for scaffold implantation. The tube is cut open, the scaffold is inserted, and the shape of the tubing returns or recovers to its original shape. TYGON® (polyvinyl chloride thermoplastic polymer) tubing is approved for many medical applications and has been shown to be biocompatible in our peripheral nervous system, with only a thin leptomeningeal layer after a 1 year implantation. If the anchoring point needs to be changed during surgery, the TYGON® (polyvinyl chloride thermoplastic polymer) tubing can easily be cut to the appropriate lip size."

"TYGON® (polyvinyl chloride thermoplastic polymer) tubing of 1 mm inner diameter and 1.5 mm outer diameter is used. A razor blade is used to cut the TYGON® (polyvinyl chloride thermoplastic polymer) tubing in a uniaxial manner. The tubing is opened and then stabilized with clamps on each side. The scaffold is then implanted using only the surface tension of the water and a flat forcept to place the scaffold into the appropriate position. The tubing clamps are removed and the TYGON® (polyvinyl chloride thermoplastic polymer) tubing returns to the original shape. A small amount of medical crazy glue may be applied along this seam to help stabilize the interface, but has not been proven to be necessary. Thus, the scaffold is anchored inside of the TYGON® (polyvinyl chloride thermoplastic polymer) tubing with an evenly distributed force. Generally, a 1 to 2 mm "lip" beyond each side of the scaffold is used for anchoring the tissue to the TYGON® (polyvinyl chloride thermoplastic polymer) tubing."

Example 5

Multifunctional Polyelectrolyte Layer Coatings

It is desirable to deploy scaffolds capable of sustained release of neurotrophic growth factors (NGF) that exhibit a high degree of biocompatibility.

Accordingly, another embodiment of the instant invention includes scaffolds coated with Multifunctional Polyelectrolyte Layers (MPL's). The MPL coatings are deposited on the surface of the scaffolds at low pH and are capable of incorporating proteins such as NGF. When the scaffolds are exposed to the body's pH near 7, the MPL coatings can be designed to degrade, thus releasing the NGF in a controlled, time-release manner. Also, surface modification of hydrogel components such as the inventive scaffolds has been shown to reduce inflammatory response, thus increasing biocompatibility.

The MPL coatings can be biodegradable or non-biodegradable. Biocompatible degradable MPL coatings on agarose hydrogel scaffolds provide two key functions. First, time-controlled NGF release over a period of weeks is possible because the growth factor, while initially bound up in the MPL layer, is released as the MPL layer biodegrades. Also, the MPL layer is cytophobic during NGF release. Upon completion of the NGF release, the surface then turns cytophilic. These two functions allow sustained release of NGF and reduce undesirable cell adhesion onto the channel walls of the scaffold to permit/enable nerve growth. In contrast, non-degradable and non-biocompatible coatings provide a permanent cytophobic coating, but are not tuned for controlled release of NGF.

MPL technology involves fabrication of sandwiched multilayers using three polymers, namely, polyethylene glycol (PEG), polyacrylic acid (PAA) and protein (such as NGF). The basic fabrication process involves the use of a technique previously developed for film fabrication, namely, a layer-by-layer assembly process (Decher, Science, 1997). Two different sets of multilayers, namely H-bonded PAA/PEG multilayers and protein/PEG multilayers are deposited at pH of 2.0 (of PEG and PAA) and pH of 3.0 (of protein) with varying individual numbers of bilayers. Alternate arrangements of these two different multilayers; with protein/PEG multilayers sandwiched between the two PAA/PEG multilayers, form the backbone structure of MPL. In other words, protein/PEG and PAA/PEG multilayers are arranged alternatively in a stacking fashion, on top of each other. The number of bilayers of individual multilayers and their overall stacking arrangement form the MPL, which are two key functions that control the sustained release of proteins. The number of bilayers is also a key function in controlling the cytophobicity or cytophilicity of these MPLs (discussed below). H-bonded PAA/PEG multilayers degrade upon immersing in neutral pH solution, and sandwiches with lower number of bilayers may degrade at a slower rate (Ono and Decher, Nanoletters, 2006). Degradation of the bilayers releases the protein along with PAA and PEG into solution. The degree of binding of protein to PEG or PAA in solution after MPL degradation would essentially depend on the isoelectric point of protein, local concentration of PAA and PEG and the salt concentrations in the solution. We fabricate 5 bilayers of protein/PEG multilayers and sandwich this multilayer between two PAA/PEG multilayers each having 5 bilayers. Protein/PEG multilayers are sandwiched for at least three consecutive cycles/times in the same MPL, thus forming at least 30 bilayers, cumulatively, in a MPL to achieve time-controlled release of required amounts of protein at the lesion site. In the present inventive design, the protein in a neurotrophic factor, although one of skill in the art will easily realize that other proteins (such as NGF) are possible.

The basic interactions employed to form MPL on agarose hydrogels are hydrophobic and H-bond interactions. To initiate the MPL formation process on the agarose matrix, a polymer with hydrophobic characteristics as well as H-bond forming capabilities, such as a branched polyethylenimine (BPEI), is required. To maintain the complete biocompatibility of the scaffolds, protein is used as the MPL initiating polymer and subsequently the sandwiched multilayers of PAA/PEG and protein/PEG (as explained above) are fabricated. BPEI is used as the initiating polymer in cases where non-degradable multilayer formation is required to achieve long term cytophobicity (discussed below). FIG. 22 shows the protein release profiles of two separate MPLs; one initiated with BPEI and other initiated with protein.

Considering that the thickness of MPL ranges between 100-500 nm, we believe that the initial phase of the multilayer deposition occurs within the intrinsic pores of the agarose gel which usually ranges from a few nanometers to a few hundred nanometers. Subsequently, in the later stages of the deposition with increasing number of bilayers, the film formation may be occurring on the outer surface of the agarose matrix.

FIG. 23 is an SEM micrograph image of a BPEI(PAA/PEG)$_5$[(PAA/BSA)$_{50}$] MPL which was fabricated onto 3% (w/v) agarose. The image was taken after 4 weeks of ambient drying of the MPL-coated agarose.

We confirmed that protein was loaded onto the hydrogel in the MPL coating process by looking for an increase in absorbance at 280 nm with increasing number of bilayers of protein/PEG bilayers on agarose hydrogel. FIG. 24 shows the change in absorbance of a BPEI(PAA/PEG)$_5$[(PAA/BSA)$_{50}$] MPL-loaded hydrogel as a function of an increasing number of PAA/BSA layers.

As discussed above, both PAA/PEG MPL's and SPS/PDAC MPL's exhibit cytophobic behavior upon deposition onto hydrogel scaffolds.

The PAA/PEG coatings provide a cytophobic surface depending on the number of bilayers. The lower the number of bi-layers, the more cytophobic the films are. These multilayers degrade over time and do not present a rigid substrate for cell adhesion. MPL coatings (PAA/PEG and protein/PEG sandwiched multilayers) also present a cytophobic (cell resistive) surface, essentially for the period in which they release the proteins from within the films. It is important to resist undesirable cell adhesion onto the channel wall of implants, while simultaneously releasing the protein from the scaffolds in a controlled manner. Depending on the number of bilayers of PAA/PEG and protein/PEG sandwiched and their arrangement, the amount of time for MPL to degrade and the cell resistant nature can be tuned. To demonstrate the cytophobic effect of the PAA/PEG MPL coatings, FIG. 25 shows fibroblast adhesion behavior on PAA/PEG multilayers deposited on a plane glass substrate.

Poly(styrene sulphonate)/Poly(diallyldimethylammonium chloride) (SPS/PDAC) represents a multilayer system which is non-biodegradable and non-biocompatible, however it provides a permanent cytophobic surface to cells depending on the number of bilayers. In contrast to PAA/PEG multilayers, we find these multilayers are cytophobic at a higher number of bilayers (30 bilayers onwards) and cytophilic at a lower number of bilayers. This cytophobic/cytophilic effect of (SPS/PDAC) multilayers does not change over time, since these films are non-biodegradable. BPEI(SPS/PDAC) multilayers may be coated onto the agarose hydrogels to provide long term cytophobicity to the adhesion of undesirable cells to the surface of the scaffold in vivo. FIG. 26 shows two micrographs of images of BPEI(SPS/PDAC) multilayer coatings fabricated onto agarose matrices. The images were taken after partial ambient drying of the agarose-multilayer structures. FIG. 27 shows fibroblast adhesion behavior on (PDAC/SPS) multilayers on a plane glass substrate.

(SPS/PDAC) multilayers are formed on agarose hydrogel scaffolds using BPEI as the initiating hydrophobic component and H-bonding polymer on the agarose matrix. Subsequently, SPS is deposited as the negative polyelectrolyte over BPEI. This is followed by the PDAC deposition. The whole process is repeated, according to the previously described layer-by-layer assembly process, until the required numbers of (PDAC/SPS) bilayers are formed. These multilayers are deposited at 0.1 M NaCl salt concentration, which is similar to the physiological level of salt concentration.

MPL's containing neurotrophic factors can be deposited on the surface of the nerve guidance implants by immersion in monomer baths for pre-determined times and in alternating sequences. Deposition typically occurs in deposition baths at a pH of 3-4, which the growth factors can typically withstand.

After coating, the surface-modified implants are sterilized and can be implanted in the body. The MPL's initiate degradation upon implantation into the lesion site, the rate of which can be controlled by the number of MPL layers, or by alternating layers of MPL's. Thus, timing and or sustaining the release of neurotrophic factors are possible with this approach. Additionally, the MPL technology is expected to improve biocompatibility by functionalizing or passivating the surface of agarose hydrogels such that they are less likely to elicit an immune response.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

The invention claimed is:

1. A method for manufacturing a biocompatible neurological platform comprising:

immersing a matrix into a first solution, the matrix comprising a first polymer surrounding a plurality of second polymer members arranged in a desired distribution pattern within the first polymer with each of the plurality of second polymer members having a predetermined length, cross-sectional area and cross-sectional shape, the first polymer being soluble in the first solution, the plurality of second polymer members being soluble in a second solution incorporating acetonitrile and insoluble in the first solution wherein the first solution dissolves the surrounding first polymer;

immersing the plurality of members in a third solution in which the plurality of members are insoluble, the third solution forming a biocompatible matrix surrounding the plurality of members;

centrifuging the plurality of members immersed in the third solution; and immersing the plurality of members and surrounding biocompatible matrix in the second solution to thereby dissolve the plurality of members and create an array of pores disposed in the biocompatible matrix, wherein the pores are defined by adjacent hollow chambers comprising walls of less than about 200 micrometer thickness, whereby the biocompatible neurological platform is formed and comprises:

a scaffold comprising a biocompatible material having first and second ends and a predetermined length;

the array of pores disposed in the scaffold and extending from the first end to the second end, wherein the pores are defined by adjacent hollow chambers comprising walls of less than about 200 micrometer thickness; and a reservoir disposed in the scaffold adapted for the time-release deployment of at least one neurotrophic agent.

2. The method of claim 1 wherein the first polymer is selected from a group of polymers comprising a polymethylmethacrylate polymer, a polystyrene polymer, and a polyvinyl alcohol polymer.

3. The method of claim 2 wherein the first solution comprises polypropylene carbonate if the selected first polymer comprises polymethylmethacrylate, and comprises tetrahydrofuran if the selected first polymer comprises polystyrene, and comprises water if the selected first polymer comprises polyvinyl alcohol.

4. The method of claim 1 wherein the plurality of second polymer members are selected from a group of polymers comprising a polymethylmethacrylate polymer, a polystyrene polymer, and a polyvinyl alcohol polymer.

5. The method of claim 4 wherein the second solution comprises polypropylene carbonate if the selected second polymer members comprises polymethylmethacrylate, and comprises tetrahydrofuran if the selected second polymer members comprises polystyrene, and comprises water if the selected second polymer members polyvinyl alcohol.

6. The method of claim 1 wherein the third solution is a biocompatible gel in liquid form.

7. The method of claim 1, wherein the biocompatible neurological platform is adapted to be surgically implanted in a spinal column.

8. The method of claim 7, further comprising placing a neurotrophic agent in at least a portion of the pores.

9. The method of claim 1 wherein the biocompatible matrix has face dimensions exceeding 1 $cm^2$ and the conduits exceed 1 cm in length.

10. The method of claim 1, further comprising the step of deploying the scaffold inside an outer reinforcing tube.

11. The method of claim 10, wherein the outer reinforcing tube is constructed of TYGON® (polyvinyl chloride thermoplastic polymer) medical tubing.

12. The method of claim 1, wherein the method includes coating the scaffold with a polyelectrolyte layer.

13. The method of claim 12, wherein the polyelectrolyte layer is a multifunctional polyelectrolyte layer.

14. The method of claim 13, wherein a neurotrophic factor is incorporated in the multifunctional polyelectrolyte layer.

15. The method of claim 13, wherein the multifunctional polyelectrolyte layer is a polyacrylic acid/polyethylene glycol multilayer.

16. The method of claim 13, wherein the multifunctional polyelectrolyte layer is a poly(styrene sulphonate)/poly(diallyldimethylammonium chloride) multilayer.

17. A biocompatible neurological platform comprising:
a scaffold comprising a biocompatible material having first and second ends and a predetermined length;
an array of pores disposed in the scaffold and extending from the first end to the second end, wherein the pores are defined by adjacent hollow chambers comprising walls of less than about 200 micrometer thickness; and
a reservoir disposed in the scaffold adapted for the time-release deployment of at least one neurotrophic agent.

18. The platform of claim 17 wherein the pores are further defined by an aspect ratio greater than 10.

19. The platform of claim 17 wherein the pores are further defined by an aspect ratio greater than 150.

20. The platform of claim 17, wherein the neurotrophic agent is selected from the group consisting of brain derived neurotrophic factor and brain derived neurotrophic factor secreting marrow stromal cells.

21. The platform of claim 17, wherein the scaffold is deployed inside an outer reinforcing tube.

22. The platform of claim 21, wherein the outer reinforcing tube is constructed of TYGON® (polyvinyl chloride thermoplastic polymer) medical tubing.

23. The platform of claim 17, wherein the scaffold is coated with a polyelectrolyte layer.

24. The platform of claim 23, wherein the polyelectrolyte layer is a multifunctional polyelectrolyte layer.

25. The platform of claim 24, wherein a neurotrophic factor is incorporated in the multifunctional polyelectrolyte layer.

26. The platform of claim 24, wherein the multifunctional polyelectrolyte layer is a polyacrylic acid/polyethylene glycol multilayer.

27. The platform of claim 24, wherein the multifunctional polyelectrolyte layer is a poly(styrene sulphonate)/poly(diallyldimethylammonium chloride) multilayer.

28. The platform of claim 17, wherein the wall thickness is less than about 100 micrometers.

29. The platform of claim 17, wherein the wall thickness is less than about 50 micrometers.

30. The platform of claim 17, wherein the wall thickness is less than about 40 micrometers.

31. The platform of claim 17, wherein the device is more than about 40 millimeters along the longest dimension of the device.

32. The platform of claim 17, wherein the device is more than about 100 millimeters along the longest dimension device.

* * * * *